Figure 1A:
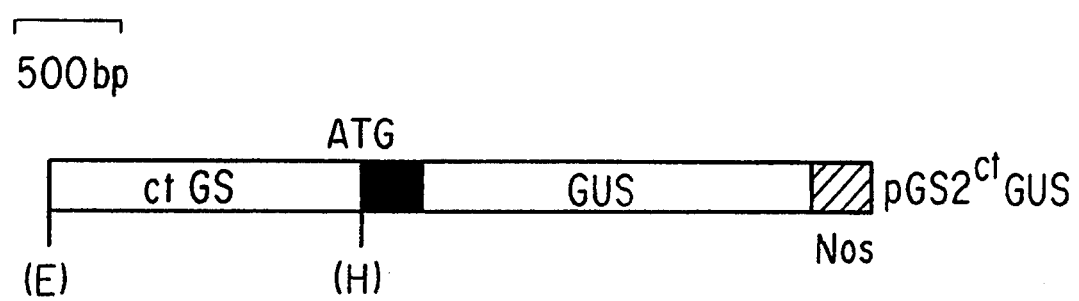

United States Patent [19]
Coruzzi et al.

[11] Patent Number: 5,391,725
[45] Date of Patent: Feb. 21, 1995

[54] ORGAN-SPECIFIC PLANT PROMOTER SEQUENCES

[75] Inventors: Gloria M. Coruzzi, New York, N.Y.; Janice W. Edwards, University City, Mo.; Elsbeth L. Walker, South Hadley, Mass.; Timothy Brears, New York, N.Y.

[73] Assignee: New York University Medical Center, New York, N.Y.

[21] Appl. No.: 715,751

[22] Filed: Jun. 13, 1991

Related U.S. Application Data

[63] Continuation-in-part of Ser. No. 448,036, Dec. 8, 1989, abandoned.

[51] Int. Cl.$^6$ .................. C07H 21/04; A01H 5/00; C12P 21/00
[52] U.S. Cl. ................... 536/24.1; 435/69.1; 435/172.3; 435/320.1; 800/205; 935/35; 935/36
[58] Field of Search ............ 536/27, 23.6, 24.1; 435/69.1, 172.3, 320.1; 800/205; 935/35, 36

[56] References Cited

U.S. PATENT DOCUMENTS

| | | | |
|---|---|---|---|
| 4,782,022 | 11/1988 | Puhler et al. | 435/172.3 |
| 4,886,753 | 12/1989 | Marcker et al. | 435/172.3 |
| 4,962,028 | 10/1990 | Bedbrook et al. | 435/172.3 |

FOREIGN PATENT DOCUMENTS

WO88/09334 12/1988 WIPO .

OTHER PUBLICATIONS

Miflin and Lee, 1982, in "Nucleic Acid and Proteins in Plants I: Structure, Biochemistry and Physiology of Proteins," eds. Boutler, D. & Parthier, B., Springer-Verlag, Berlin Heidelberg N.Y., pp. 5–64.
McNally et al., 1983, Plant Physiol. 72: 22–25.
Kern and Chrispeels, 1978, Plant Physiol. 62: 815–819.
Winter et al., 1982, Plant Physiol. 69: 41–47.
Wallsgrove et al., 1983, Plant Cell Environ. 6: 301–309.
Wallsgrove et al., 1987, Plant Physiol. 83: 155–158.
Miflin, 1974, Plant Physiol. 54: 550–555.
Robertson et al., 1975, Aust. J. Plant Physiol. 2: 265–272.
Lara et al., 1983, Planta 157: 254–258.
Hirel and Gadal, 1980, Plant Physiol. 66: 619–623.
Hirel et al., 1987, EMBO J. 6: 1167–1171.
Tingey et al., J. Biol. Chem. 263(20): 9651–9657 (1988).
Tingey et al., EMBO J. 6: 1–9 (1987).
Forde et al., 1989, Plant Cell 1: 391–401.
Gebhardt et al., 1986, EMBO J. 5: 1429–1435.
Edwards & Coruzzi, 1989, Plant Cell 1: 242–248.
Cullimore et al., 1984, J. Mol. Appl. Genet. 2: 589–599.
Tingey and Coruzzi, 1987, Plant Physiol. 84: 366–373.
Coruzzi et al., 1984, EMBO J. 3: 1671–1679.
Herrera-Estrella et al., 1984, Nature 310: 115–120.
Apel et al., 1978, Eur. J. Biochem. 85: 581–588.

(List continued on next page.)

Lewin, ed., "Genes", 2nd Edition (1985) by John Wiley & Sons, pp. 469–470.
Edwards et al., PNAS USA 87: 3459–3463 (1990).

*Primary Examiner*—Patricia R. Moody
*Attorney, Agent, or Firm*—Pennie & Edmonds

[57] ABSTRACT

The present invention relates to novel plant organ-specific transcriptional promoter nucleic acid sequences, which regulate the expression of glutamine synthetase isoenzymes. Specifically, promoter sequences were isolated from the nuclear gene for chloroplast GS2 glutamine synthetase and from two nuclear genes for cytosolic GS3 glutamine synthetase in the pea plant, *Pisum sativum*. Accordingly, the present invention provides for the nucleic acid sequences of the GS2, GS3A and GS3B promoter sequences as well as functional portions thereof.

The invention further provides for promoters homologous to GS2, GS3A and GS3B, or any portion thereof as well as gene fusions and transgenic plants in which genes that encode heterologous proteins are controlled by the promoter sequences of the invention.

30 Claims, 33 Drawing Sheets

OTHER PUBLICATIONS

Stiekema et al., 1983, Plant Physiol. 72: 717–724.
Thompson et al., 1983, Planta 158: 487–500.
Jones et al., 1985, EMBO J. 4: 2411–2418.
Stockhaus et al., 1989, Plant Cell 1:805–813.
Gurley et al., 1986, Mol. Cell. Ciol. 6: 559–565.
Landsmann et al., 1988, Mol. Gen. Genet. 214: 68–73.
Bevan et al., 1989, EMBO J. 8: 1899–1906.
Benfey and Chua, 1989, Science 244: 174–181.
Rocha-Sosa et al., 1989, EMBO J. 8: 23–29.
Ha and An, 1989, Nucleic Acids Res. 17: 215–224.
An et al., 1988, Plant Physiol. 88: 547–552.
Schmulling et al., 1989, Plant Cell Physiol. 30: 649–653.
Sugaya et al., 1989, Plant Cell Physiol. 30: 649–653.
Odell et al., 1985, Nature 313: 810–812.
Jensen et al., 1986, Nature 321: 669–674.
Jefferson et al., 1987, EMBO J. 6: 3901–3907.
Sanders et al., Natl. Acids, Res. 14: 1543–1558. (No Date?).
Benfey et al., 1989 EMBO J. 8: 2195–2202.
Novitski et al., 1984, Current Genetics 8: 135–146.
Haucke et al., 1988, Current Genetics 14: 471–476.
Netzker, 1982, Nucleic Acids Res. 10(15): 4783–4794.
Stalker, 1988, Science 242: 419–423.
Cuozzo, 1988, Bio/Technology 6: 549–557.
Coruzzi, 1987, "Molecular Analysis of Glutsamine Synthetase Genes in Higher Plants" in Plant Gene Systems and their Biology 62: 217–226, Alan R. Liss, Inc.
Walker and Coruzzi, J. Cell. Biochem. (Supple) 12C: 206 Abstract No. L530 (1988).
Coruzzi et al., J. Cell Biochem (Supple) 12C: 153 Abstract No. L053 (1988).

FIG. 5A-1

```
5' GAATTC AGAAAGGAAA GGGAAAGACT CTTCAGATGT TGGAAGCAAG GAAGAGGCCT
   EcoRI         10         20          30          40         50

ATATAAAGGA CATGAAGAAA TGAGGAATAT GTGGGGCAG  AATCACATGA
        60         70          80          90        100
                                            (position 90: GTGGGGCAG)
```

| | 10 | 20 | 30 | 40 | 50 |
|---|---|---|---|---|---|
| 5' GAATTC | AGAAAGGAAA | GGGAAAGACT | CTTCAGATGT | TGGAAGCAAG | GAAGAGGCCT |
| EcoRI | 60 | 70 | 80 | 90 | 100 |
| | ATATAAAGGA | CATGAAGAAA | TGAGGAATAT | GTGGGGCAG | AATCACATGA |
| | 110 | 120 | 130 | 140 | 150 |
| | GAAAATACTT | GAATACACTT | AAATCAATTA | TTTTTATACT | CTCCTTGACG |
| | 160 | 170 | 180 | 190 | 200 |
| | AATAACGGGG | AAGTCAACCT | TTTAGTATTT | TTACCAAGAA | TACACAAATA |
| | 210 | 220 | 230 | 240 | 250 |
| | AATAGAATCT | AATTCTTTTA | ATAGAAATCA | ATTATCGGAG | TCACACAATT |
| | 260 | 270 | 280 | 290 | 300 |
| | GCTGCGATTA | ATTTCTCGAG | TAGAATTTGA | TTAAAACTAA | ATATACATAA |
| | 310 | 320 | 330 | 340 | 350 |
| | ATGAGTGAGA | ACACCAAATA | AATAAAATTA | TAAAAAAATAA | TATTATAATG |
| | 360 | 370 | 380 | 390 | 400 |
| | TATTAAGATG | ATAAAGTATA | ATTAACTTTA | GACTTAAATG | AGTTTTTTTT |
| | 410 | 420 | 430 | 440 | 450 |
| | TTACTCTTCC | ATTATTTTAT | TTGGAGTTTC | CCCCCATTTT | TTAAATCCCA |
| | 460 | 470 | 480 | 490 | 500 |
| | AAATAATGTT | ACTTATGTGC | TAATTTGTCA | AATCATAGTT | TTGATATTAA |
| | 510 | 520 | 530 | 540 | 550 |
| | AATTTTCAA  | TATATTGTAA | TGCTACATAA | GTTTCACGTG | CATTATTTCT |
| | 560 | 570 | 580 | 590 | 600 |
| | CAATCATCAT | ATTTACTACT | AAATGTTAAA | ATTTGACATA | GAAATCAAAA |
| | 610 | 620 | 630 | 640 | 650 |
| | TTGTATAAAT | TCAAAAACTA | TATAATCATA | ATTGCAAATT | AATGTTTCTA |

```
 660 AGCAAAGCAA  670 CTTAAGTTAA  680 GAAGATCTAA  690 GCAAAGATAC  700 AAAGATATTG
 710 TCAACATAGA  720 ATTTAGTAAT  730 CATTATTCAT  740 TGTAGTTATA  750 GAATCTAAAC
 760 ATGAAAATTA  770 ATTGGATAAA  780 AAAAGAAAGA  790 GAAATCCTTA  800 TCTAAATATT
 810 GAAAGTCCAA  820 GCTTCTCTTG  830 GTGCTCTTTA  840 AGGGACCAAA  850 AACAAACTTC
 860 ATCCACTCAA  870 AAACTCACCC  880 CTATCGTTAT  890 TGCAATAGCC  900 AACAAACTTG
 910 TTTTCTTGCC  920 CACCACCAAC  930 CCTTATTTTA  940 CACAACTCTC  950 TCTCACTCTC
 960 TATTGCTCCA  970 TTGACACAAG  980 GCTCATTCTC  990 ACTTGAACCC 1000 ATTTTCAACC
1010 TTTGCTGTTT 1020 TTGCCATTTT 1030 TCAACTCTGT 1040 ATGGGTGAGT 1050 TTCTTTCTAC
1060 CTTCAATACC 1070 ATTTTCGTCC 1080 TTTTTCTTAA 1090 ACGTTTATTT 1100 ATGACATTCA
1110 AAATTCAATC 1120 TTTGTAGTTT 1130 CTTGCTAGTG 1140 AAAATTTATG 1150 ATGGTTCTTT
1160 GAATATACTT 1170 TAGCTTCATG 1180 CAAAACTAAC 1190 TTCTTTATCA 1200 TTTGAGCAA
1210 ATTGATGTTT 1220 AGTAGCTATG 1230 AAAGAATTTG 1240 GATCTGATTA 1250 ATCACTTTGT
```

FIG. 5A-2

```
1260        1270        1280        1290        1300
TTTATTGTGT  TATATCTAAA  TATGATTCCA  AAAAGCAATG  CTCTTGGTAA
        1310        1320        1330        1340        1350
ACTTTACTCT  CTTTTATGTT  AGTTAGATAT  TTCTTGAAT   GATTATTTAC
        1360        1370        1380        1390        1400
TTCTTGGTTG  GTTTTTTGCA  ATGTGCATCT  TAATAGAATG  CTGTTTGATT
        1410        1420        1430        1440        1450
CTTTTTTTT   TTGTTGAGTA  GAAAATGGCG  CAGATTTTGG  CACCCTTCGAC
        1460        1470 MET 1480       1490        1500
GCAATGGCAG  ATGAGAATCA  CAAAAACCTC  TCCTTGTGCA  ACTCCAATCA
        1510        1520        1530        1540        1550
CATCAAAGAT  GTGGAGTTCT  TGGTTATGA   AACAAACTAA  GAAAGTTGCG
        1560        1570        1580
CATTCTGCTA  AATTTAGAGT  TATGGCA GTC AAC
                                HincII
```

FIG. 5A-3

```
-1832  GATCCCTCTAG  CCTATCAAGG  AGTAATATCT  ATCATATCTA  ACTCTGGACC  CATTTACTTG
-1772  GATCTAGTTA  GAGAATTTTA  TGTAAATTTA  TCAATTGGTA  CTGGGTGCAT  TTTGTAATCA
-1712  AAAGTGAAGG  ACAAAAATAC  TGTAAATTTA  TCAATTGGTA  ATGGACATGA  CAAAGTACCT
-1652  AATTCACCCC  TCCCTCCTCT  TAGGTGCATT  CCATACTTAC  AATAGTTTAT  ATAATTGGAT
-1592  TGGACATAAC  ATCGATGGTG  GCTCTACCTT  TTTGTTGCT  TGCTGATAGT  TGCGTTGCGC
-1532  TAGGAACAAA  TTGTGTCTTG  CTAATGAAAT  TGTATCTTCA  TATACTTTGA  AACTCATAAC
-1472  AATGAATTGT  GCTAATCTGT  TAGCTAAATG  TTTTCTCAAG  CAGTGTCTTA  TCTAATTAGA
-1412  ACGATCACGT  GGAATGCACA  CAAAGGTAGT  AATATAATTT  TGAATGTTAA  TGACAGTAGC
-1352  CTCAGTAATC  CCGACGTCTC  AAGTTTTGGT  GGGTTGATTT  GAAGTGTTGA  TGGTGTTTGG
-1292  GTTCACGATT  TTGTGGGTAA  TATTGGTTAT  TCCAATATCC  TTCATGTTGA  GTGATTGCAT
-1232  TATATCATGC  TTTGTGTATG  ACCTAAAAAC  TGGCCCAGTG  AAGACTTGAG  GTGTTATTCT
-1172  AACTCCAACT  CTATTATCA  GCTTATCACA  TTGGTCGGTTA  ATGTTTAACA  TCACTGTGCT
-1112  GCTAATCTTC  ACAATATTAA  AAAACTGGTC  TCTTAGGAAT  GCCGGGTTCA  AATATTTCTA
-1052  CTCTTAGGAA  GAAGAATGTT  TGTGTTGACT  ATCAGCAAA  ACATGGAACT  GACAATGATG
-992   CGGCGTACCA  GTCTTTTGCA  GAGCCTACTA  TAGGAATCAT  CACTCACTTA  CTAGTTGGCG
-932   CTAGTGAGAT  TTTATTTTT  AAATAATTT  TTTTCTTTTC  CTTTTTTACT  TGTACAAAAA
-872   AAATATTCAA  GTTCAAAAAA  AAAGAAAAAA  AATTATTGA  ATTTAAAATA  AAAATCAAAA
-812   ATGAAAAATC  AAATAAAAATA  GAGAACACTA  AATTATTTTA  AATTCTTTTA  TTAAATACAT
-752   GAATAAAAAC  TAAATAATAT  AATAATGATC  TTTCAATTA  AATACTAATT  CATATAATAA
-692   TAAAAACTAA  CTATAAGAAT  ACTAACAATA  AACTTTAATT  GCTTATTAA  GTCATCTATA
-632   ATAGAGAAAT  TCAATAATAA  CAAGTTTGAA  TTGTGAAATT  TTGATTATTA  GATACTAAAG
-572   AGTGAAATTT  TAATTATTAG  ATATTAATA  AAAATATTAT  TTTAAAATAG  TATACTTTAA
-512   TTTGAATTAA  TATTTAAAGT  TGTATTACAT  AGAACTTTAA  AAATGCTAAA  TAAAATTATT
-452   TTGAATCAAA  ATATAAAATA  AATATTAATA  AGTTTTACCA  AAAAAAAAAT  ATTAATTAAG
-392   TGAAGTATCC  TACCAACCAC  ATATAAATTA  GATAATTATA  TTAAAAACA  TACTTTTCCG
-332   TACATTGCTT  CTCATTAAAA  TATCATTTAT  CTATAAGACA  GAATCATATC  TACACCGCAA
```

FIG. 5B-1

```
-272  ATTATTCTCA  TTAGATTCGT  AAAGAAATT   CAAAGTTATC  ATATCCTTTC  CTTTTCTTTT
-212  AGAAAAAAT   TAAGTGATAA  TCTATTTTAT  TTCATTTCTA  TCTTTAAGAA  ATTAAAAAT
-152  AACCATTTTA  TTCCAATTTT  CAAAATTCAA  TTGATCTAGT  AGATAAAAG   ATTCTCCGAA
 -92  GACAACCACT  AAAAGTTAA   TAACAATTTA  ATAGTAATTT  TTTCTACATA  TCATTCTATT
 -32  ATAAATAGGT  TCATATCTCA  CACTTTCTTT  TAaCCCTTAC  AAAAAGCCAG  AGATTCCTCT
 +29  GTAGCTATCT  TTCAACAAAA  CCGCGTTCTT  CTTTTTCCTT  CAAAGCTTTT  CATTATCATT
 +89  ATGTCTTCAC  TTTCAGATC
                  +107
```

FIG. 5B-2

FIG. 5C-1

```
     Pst I      10           20           30           40           50
5' CTGCAGAATA TGACTATGGG CTCTAAAGAA AGCTTCAAAG AATATGCTCA
              60           70           80           90          100
   AAAATGGAGA GACTTGGCTG ACAGAGTCAA ACCCCCTATG ACTGATCGAG
             110          120          130          140          150
   AATTAGTGGA CATGTTCATG GGTACACTGA CTGGCCCATT CTACAGCCAT
             160          170          180          190          200
   ATATTGGGAA GTTCCTCATC GGGTTTCACT GAACTTATAT TTACGGGTGA
             210          220          230          240          250
   ACGTGTTGAA CGCGGCATTC GAAGTGGAAA GATACATGCG GCTACCTCTG
             260          270          280          290          300
   CAAGCACAAA AAAGTCCTAT CAAGGGAAGA ATGAATCAAA TGCTGTGTAC
             310          320          330          340          350
   GGTCAAAGGG GTCATAACAA GAAAAATCGT GACCATACTG TTGGAGCAGT
             360          370          380          390          400
   TACGATTGCA GCACCGCCAT CTCAAAACTT CCAACACACA CAAGACAGGC
             410          420          430          440          450
   CAAGAAGGCA GTTTACCAAG ATCAATATGA CTTTAGCACA AGCACTGTAG
             460          470          480          490          500
   GGTATGCTAA AAGCAAATTT AATTACCCTC AGAGATCCTC CTGCAAATCC
             510          520          530          540          550
   CAACACTACT TCTCCTCGTT ATAATCCCAA TGCCAGGTGT GCATATCACT
             560          570          580          590          600
   CCGATAGCCC CGGGCATGAT ACAAACGATT GTTGGTTGTT GAAGAATAAG
             610          620          630          640          650
   ATTCAGGATA TGATCGACGC TGGAGAAATT GAATTTGATC CTTCGGAGAC
```

FIG. 5C-2

| | | | |
|---|---|---|---|
| 660 | 670 | 680 | 690 | 700 |
| TCCTAATGTC | ATCACTGCTC | CAATGCCTAA | TCATAACAAG | ACTATTAATG |
| 710 | 720 | 730 | 740 | 750 |
| TTGTGGATGA | CATACTTAAA | AAATATTCTT | TTTCATACAT | ATTAATTAAA |
| 760 | 770 | 780 | 790 | 800 |
| TGAAGTATCC | TACCAACCAC | ATATTAATTA | AATAATTATA | TTAAAAAAGA |
| 810 | 820 | 830 | 840 | 850 |
| TACTTTTTCA | TACATTGCTT | CTCATAAAAA | TATCATTTAT | CTATAAGACA |
| 860 | 870 | 880 | 890 | 900 |
| GAATCATATC | TACACCGCAA | ATTATTCTCA | TTAGATTCAT | AAAAGAAATT |
| 910 | 920 | 930 | 940 | 950 |
| CAAAGTTATC | ATATCCTTTC | CTTTTCTTTT | AGAAAAAAAT | TAAGTGATAA |
| 960 | 970 | 980 | 990 | 1000 |
| TCTATTTTAT | TTCATTTCAA | TCTTTAAGAA | ATTAAAAAAT | AACCATTTTA |
| 1010 | 1020 | 1030 | 1040 | 1050 |
| TTCAATTTTC | AGAATTCAAT | TCATCTAGTA | GATAAAAAGA | TTCTCCTAAC |
| 1060 | 1070 | 1080 | 1090 | 1100 |
| ACAACCACTA | AAAAGTTAAT | ATCAATTTAG | TAGTAATTTT | TTCTACATAT |
| 1110 | 1120 | 1130 | 1140 | 1150 |
| CATTCTATTA | TAAATAGGTT | CATATCTCAC | ACTTTCTTTT | AACCCTTACA |
| 1160 | 1170 | 1180 | 1190 | 1200 |
| AAAAGCCAGA | GATTCCTCTG | TAGCTATCTT | TCAACAAAAC | GGGTTCTTCT |
| 1210 | 1220 | 1230 | 1240 | |
| TTTTTCTTCA | AAGCTTTTCA | TTATCATTAT | GTCTTCACTT | TCAGATCT 3' |
| | | | MET | BglII |

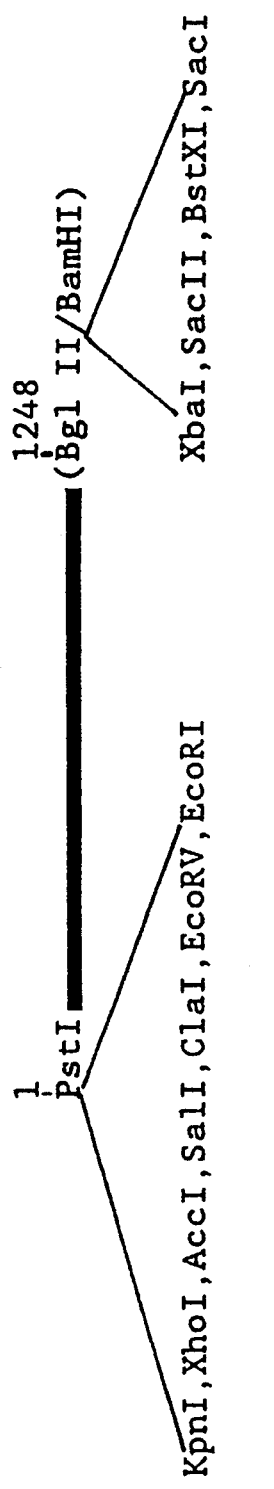
FIG. 6C

ORGAN-SPECIFIC PLANT PROMOTER SEQUENCES

The present application is a continuation in part of application Ser. No. 07/448,036, filed Dec. 8, 1989, now abandoned, which is incorporated by reference herein in its entirety.

The invention described herein was supported in whole or in part by a grant from the National Institutes of Health.

TABLE OF CONTENTS

1. INTRODUCTION
2. BACKGROUND OF THE INVENTION
   2.1. The Glutamine Synthetase System
   2.2. Plant Promoter/Enhancer Sequences
3. SUMMARY OF THE INVENTION
   3.1. Abbreviations
4. DESCRIPTION OF THE FIGURES
5. DETAILED DESCRIPTION OF THE INVENTION
   5.1. Identification Of Promoter Elements Associated With Glutamine Synthetase Genes
   5.2. Novel Glutamine Synthetase Promoter Elements
   5.3. Gene Fusions Containing Glutamine Synthetase Promoter Elements
   5.4. Creation Of Transgenic Plants Containing Recombinant Glutamine Synthetase Promoter Elements
   5.5. Utility Of The Invention
6. EXAMPLE: IDENTIFICATION OF MESOPHYLL-SPECIFIC AND PHLOEM-SPECIFIC PROMOTER ELEMENTS
   6.1. Materials and Methods
      6.1.1. Isolation of Glutamine Synthetase Genomic Clones
      6.1.2. Construction of Plasmids and Transformation of Agrobacterium
      6.1.3. Transformation and Growth of Transgenic Tobacco Plants
      6.1.4. Determination of Beta-Glucuronidase Expression
      6.1.5. Plant Growth Conditions for Light Induction Experiments
      6.1.6. Isolation of RNA and Ribonuclease Protection Assay
   6.2. Results
      6.2.1. Construction of GS-GUS Reporter Gene Fusions and Quantification of Beta-Glucuronidase Activity In Transgenic Plants
      6.2.2. The Promoter for Chloroplast GS2 Directs GUS Expression Specifically in Photosynthetic Cell Types
      6.2.3. The Promoter for a Cytosolic GS Gene Directs GUS Expression Exclusively In Phloem
      6.2.4. Expression of the GS-GUS Fusions in Germinating Transgenic Tobacco Seedlings
      6.2.5. The Chloroplast GS2 Promoter Confers Light-Regulated Expression On The GUS Reporter Gene
   6.3. Discussion
7. EXAMPLE: IDENTIFICATION OF A REGION OF THE GS3A PROMOTER REQUIRED FOR EXPRESSION IN TRANSGENIC PLANTS AND A DNA-BINDING PROTEIN WHICH BINDS TO THIS GS3A ELEMENT
   7.1. Materials and Methods
      7.1.1. DNA Cloning and Sequencing
      7.1.2. S1 Nuclease Mapping
      7.1.3. Construction Of Promoter-GUS Fusions
      7.1.4. Plant Transformations
      7.1.5. Analysis Of GUS Expression
      7.1.6. DNA Mobility Shift Analysis
   7.2. Results
      7.2.1. GS3A Promoter Sequence And Determination Of The Transcriptional Start Site
      7.2.2. Deletion Analysis Of The GS3A Promoter In Transgenic Alfalfa And Tobacco
      7.2.3. A DNA Element Within The GS3A-132 Promoter Binds To A Factor Present In Plant Extracts
   7.3. Discussion
8. DEPOSIT OF MICROORGANISMS

1. INTRODUCTION

The present invention relates to novel plant organ- and cell-type specific transcriptional promoter nucleotide sequences which regulate the expression of genes encoding glutamine synthetase isoenzymes. In particular, one promoter sequence which responds to light and two promoter sequences which are selectively active in plant vascular elements have been cloned and characterized. The promoter sequences of the invention may be used to control the expression of glutamine synthetase as well as genes encoding heterologous proteins, and may advantageously be used to render plants resistant to herbicides or viral or pathogen infection.

2. BACKGROUND OF THE INVENTION

2.1. The Glutamine Synthetase System

In higher plants, many steps in nitrogen metabolism occur in multiple subcellular compartments. For example, isoenzymes for many amino acid biosynthetic enzymes are located in the cytosol, as well as in the mitochondria or chloroplasts. The significance of this multiplicity and compartmentalization of plant isoenzymes has yet to be fully understood. The relative function of many amino acid biosynthetic isoenzymes has been difficult to assess due to inadequate fractionation of organelle and cytoplasm components, overlapping activity profiles, and immunological cross-reactivity (Miflin and Lea, 1982, in "Nucleic Acid and Proteins in Plants I: Structure, Biochemistry and Physiology of Proteins," eds. Boulter, D & Parthier, B, Springer-Verlag, Berlin Heidelberg New York, pp. 5–64). Consequently, it is unclear whether these isoenzymes carry out redundant or distinct roles in plant metabolism.

The best studied example of a plant amino acid biosynthetic enzyme shown to occur as multiple isoforms is glutamine synthetase (GS) (EC 6.3.1.2) (McNally et al., 1983, Plant Physiol. 72:22–25). Early biochemical data revealed that GS functions in the assimilation of ammonia generated by numerous plant processes which include seed germination (Kern and Chrispeels, 1978, Plant Physiol. 62:642–647; Winter et al., 1982, Plant Physiol. 69:41–47), photorespiration (Wallsgrove et al., 1983, Plant Cell Environ. 6: 301–309; Wallsgrove et al., 1987, Plant Physiol. 83:155–158), nitrite reduction (Miflin, 1974, Plant Physiol. 54: 550–555), nitrogen-fixation in root nodules (Robertson et al., 1975, Aust. J. Plant Physiol. 2:265–272; Lara et al., 1983, Plants 157: 254–258), and primary ammonia assimilation from the soil (Hirel and Gadal, 1980, Plant Physiol. 66:619–623). An analysis of the GS genes in several species has revealed a strong correlation of individual GS gene expression with specific aspects of plant development (Tingey et al., 1987, EMBO J. 6:1–9; Tingey et al., 1988, J. Bio. Chem. 263:9651–9657; Hirel et al., 1987, EMBO J. 6:1167–1171; Forde et al., 1989, Plant Cell 1:391–401; Gebhardt et al., 1986, EMBO J. 5:1429–1435; Edwards and Coruzzi, 1989, Plant Cell 1:241–248). Recent sequence analysis of GS cDNAs from Pisum sativum and Phaseolus vulgaris has shown that chloroplast and cytosolic GS are encoded by separate but similar nuclear genes (Tingey et al., 1987, EMBO J. 6:1–9; Tingey et al., 1988, J. Bio. Chem. 263:9651–9657; Cullimore et al., 1984, J. Mol. Appl. Genet. 2:589–599).

In pea, the single nuclear gene for chloroplast GS2 is expressed predominantly in leaves in a light-dependent fashion (Tingey et al., 1988, J. Bio. Chem. 263:9651–9657; Edwards and Coruzzi, 1989, Plant Cell 1:241–248). The role of chloroplast GS2 in the reassimilation of photorespiratory ammonia is supported by the analysis of mutants in barley (Wallsgrove et al., 1987, Plant Physiol. 83:155–158), and is substantiated by gene expression studies in pea (Edwards and Coruzzi, 1989, Plant Cell 1:241–248). For cytosolic GS, molecular studies have revealed the presence of a number of distinct isoforms in several plant species (Tingey et al., 1988 J. Bio. Chem. 263:9651–9657; Hirel et al., 1987, EMBO J. 6: 1167–1171; Gebhardt et al., 1986, EMBO J. 5:1429–1435; Tingey and Coruzzi, 1987, Plant Physiol. 84:366–373). In pea it has been shown that two classes of genes encode homologous but distinct cytosolic GS isoforms (Tingey, 1988, J. Bio. Chem. 263:9651–9657). One class comprises a pair of "twin" GS genes (GS3A and G3B) whose expression is specifically induced in two developmental contexts where large amounts of ammonia are mobilized for plant growth, during germination and nitrogen fixation.

2.2. Plant Promoter/Enhancer Sequences

A number of plant promoter enhancer/sequences have been identified, including light-responsive promoter sequences such as ribulose bisphosphate carboxylase (Coruzzi et al., 1984, EMBO J. 3:1671–1680; Herrera-Estrella et al., 1984, Nature 310:115–120), the chlorophyll a/b binding protein (Cab) of the light-harvesting chlorophyll-protein complex (Apel et al., 1978, Eur. J. Biochem. 85:581–588; Stiekema et al., 1983, Plant Physiol. 72:717–724; Thompson et al., 1983, Planta 158: 487–500; Jones et al., 1985, EMBO J. 4:2411–2418) and the ST-LS1 gene of potato (Stockhaus et al., 1989, Plant Cell 1:805–814). Additional plant promoter sequences include the soybean heat shock protein hsp17.5-E or hsp17.3-B promoters (Gurley et all, 1986, Mol. Cell Biol. 6:559–565); the Parasponia andersoni hemoglobin promoter (Landsmann et al., 1988, Mol. Gen. Genet. 214:68–73); the phenylalanine ammonia-lyase promoter, which appears to be active in specific cell types which accumulate phenylpropanoid derivatives in response to wounding and also during normal development of the xylem and flower (Bevan et al., 1989, EMBO J. 8:1899–1906); and the petunia 5-enolpyruvylshikimate-3-phosphate synthase gene promoter (Benfey and Chua, 1989, Science 244:174–181). Certain plant promoters, such as patatin, have also been shown to function in specialized organs such as tubers (Rocha-Sosa et al., 1989, EMBO J. 8:23–29).

Certain bacterial promoters have been observed to be expressed in plants, including the Rhizobium meliloti FIXD gene promoter described in U.S. Pat. No. 4,782,022, issued Nov. 1, 1988, by Puhler et al., and the nopaline synthase promoter (Ha and An, 1989, Nucleic Acids Res. 17:215–224; An et al., 1988, Plant Physiol. 88:547–552). Several promoter sequences, termed the rol A, B and C promoters, have been identified in Agrobacterium rhizogenes (Schmulling et al., 1989, Plant Cell 1:665–670; Sugaya et al., 1989, Plant Cell Physiol. 30:649–654). The rol C promoter described by Sugaya et al. (supra), located on the bacterial Ri plasmid, has been observed to be expressed in phloem cells.

Viral genes which are expressed in plants include the cauliflower mosaic virus (CaMV) 35S promoter (Odell et all, 1985, Nature 313:810–812; Jensen et al., 1986, Nature 321:669–674; Jefferson et al., 1987, EMBO J. 6: 3901–3907; and Sanders et al., 1987, Nuc. Acids Res. 14:1543–1558). Within the CaMV 35S promoter, expression conferred by domain A ($-90$ to $+8$) was found to be particularly strong in root tissue, whereas expression conferred by domain B ($-343$ to $-90$) appeared to be strongest in the cotyledons of seeds and seedlings and in the vascular tissue of the hypocotyl (Benfey et al., 1989 EMBO J. 8:2195–2202).

3. SUMMARY OF THE INVENTION

The present invention relates to novel plant organ-specific transcriptional promoter nucleotide sequences which regulate the expression of genes encoding glutamine synthetase isoenzymes. Specifically, promoter sequences were isolated from the nuclear gene for chloroplast GS2 glutamine synthetase and from two nuclear genes for cytosolic GS3 glutamine synthetase in the pea plant, Pisum sativum. Accordingly, the present invention provides for the nucleic acid sequences of the GS2, GS3A and GS3B promoter sequences as well as functional portions thereof.

The invention further provides for promoters homologous to GS2, GS3A and GS3B, gene fusions comprising the novel glutamine synthetase promoters, and transgenic plants which comprise the promoters of the invention.

Experiments which tested the activity of the GS2, GS3A and GS3B promoter sequences revealed that the GS2 promoter was inducible by light and directed high levels of transcription in photosynthetic cells of leaves. In addition, the GS2 promoter directs expression in nonphotosynthetic cells of the root tip. GS3A was found to be selectively active in phloem; therefore, GS3A represents the first plant-derived, phloem-specific promoter element. In various embodiments of the invention, the GS2, GS3A, and GS3B promoter sequences may be used to control the expression of glutamine synthetase as well as heterologous proteins in a tissue specific and/or light-inducible manner, The resulting tissue-specific expression of a desired gene product presents a wide range of potential applications for the promoter sequences of the invention, including, but not limited to, the manipulation of nutritional requirements and the induction of resistance to herbicides or pathogens.

3.1. Abbreviations transgenic plant: a plant which has incorporated a foreign gene into its genome transgene=transgenic sequence: a foreign gene which has been incorporated into a transgenic plant

4. DESCRIPTION OF THE FIGURES

Figure 1B:
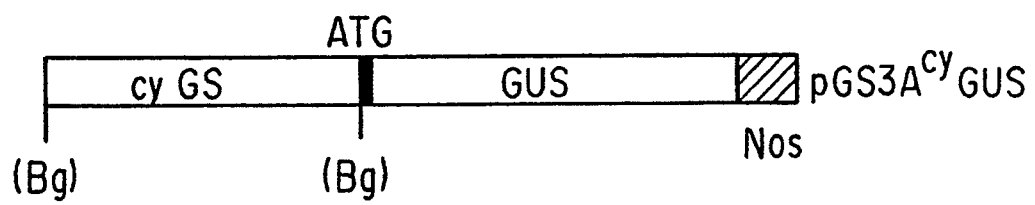

FIGS. 1A and 1B: GS-GUS Translational Fusions. 1A) pGS2$^{ct}$-GUS contains 1.5 kb of the gene for chloroplast GS2 in a translational fusion with the GUS gene of pBI101.2. 1B) pGS3A$^{cy}$-GUS contains 1.01 kb of the gene for cytosolic GS3A in a translational fusion with the GUS gene of pBI101. A 3' polyadenylation region from the nopaline synthase gene is present in both GS-GUS constructs and is denoted with diagonal stripes. The white areas represent the 5' noncoding region of each GS gene. The solid black areas depict GS coding regions and the dotted area marks the GUS coding region.

Restriction sites: E=EcoRI, H=HincII, Bg=BglII. Restriction sites in parenthesis indicate original sites in plant genes which were destroyed in plasmid construction.

Figure 2A:
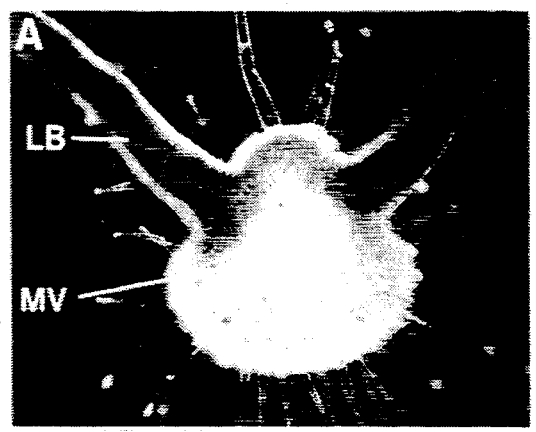
Figure 2B:
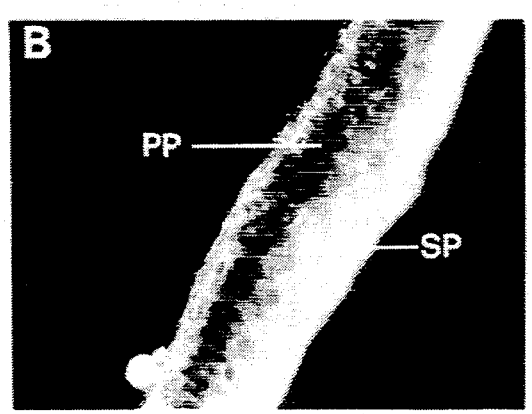
Figure 2C:
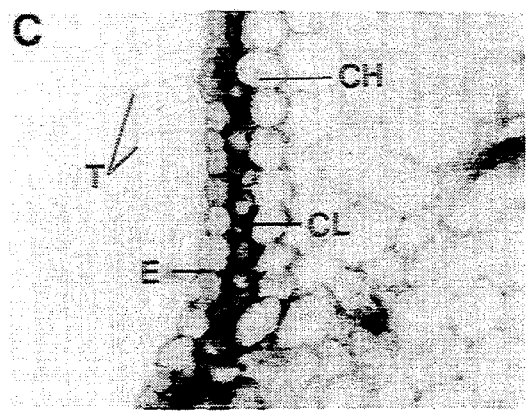
Figure 2D:
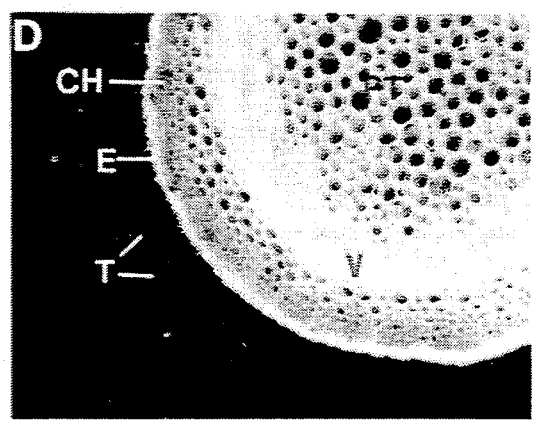
Figure 2E:
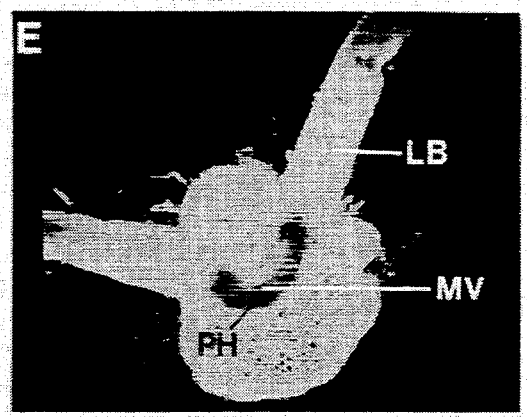

FIGS. 2A, 2B, 2C, 2D, 2E, 2F, 2G and 2H: Histochemical localization of GUS activity in cross sections of mature transgenic tobacco plants. Panels FIGS. 2A, 2B, 2C and 2D represent sections from pGS$^{ct}$-GUS transformants; FIG. 2A) leaf cross section, FIG. 2B) leaf blade cross section, FIG. 2C) leaf midrib cross section, FIG. 2D) stem cross section. FIGS. 2E, 2F, 2G and 2H represent sections from pGS3A$^{cy}$-GUS transformants: FIG. 2E) leaf cross section, FIG. 2F) leaf midrib cross section, FIG. 2G) root cross section, FIG. 2H) stem cross section. Abbreviations: CH—chlorenchyma, CL—collenchyma, E—epidermis, LB—leaf blade, MV—midvein, PH—phloem, PP—palisade parenchyma, PT—pith parenchyma, R—root, SP—spongy parenchyma, T—trichome, V—vasculature, X—xylem.

Figure 3A:
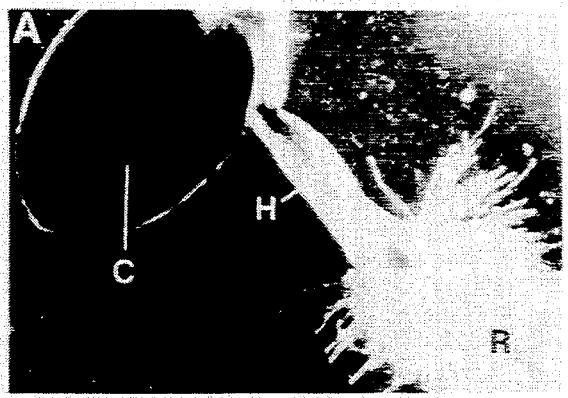
Figure 3B:
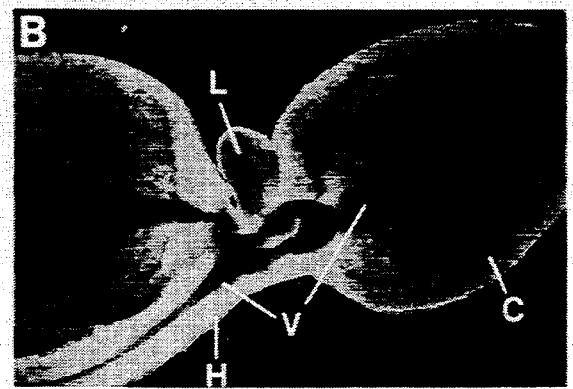
Figure 3C:
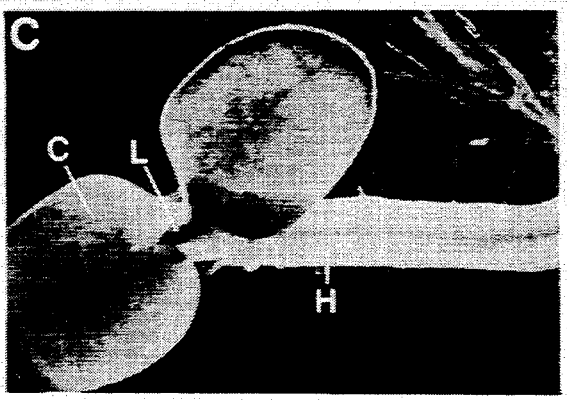

FIGS. 3A, 3B, and 3C Histochemical localization of GUS activity in whole mounts of 7 day-old transgenic tobacco seedlings; FIG. 3A) pGS2ct-GUS transformant. FIG. 3B) pGS3A$^{cy}$-GUS transformant. FIG. 3C) control, pBI101 transformant. Abbreviations: C—cotyledon, H—hypocotyl, L—leaf, R—root, V—vasculature.

Figure 4:
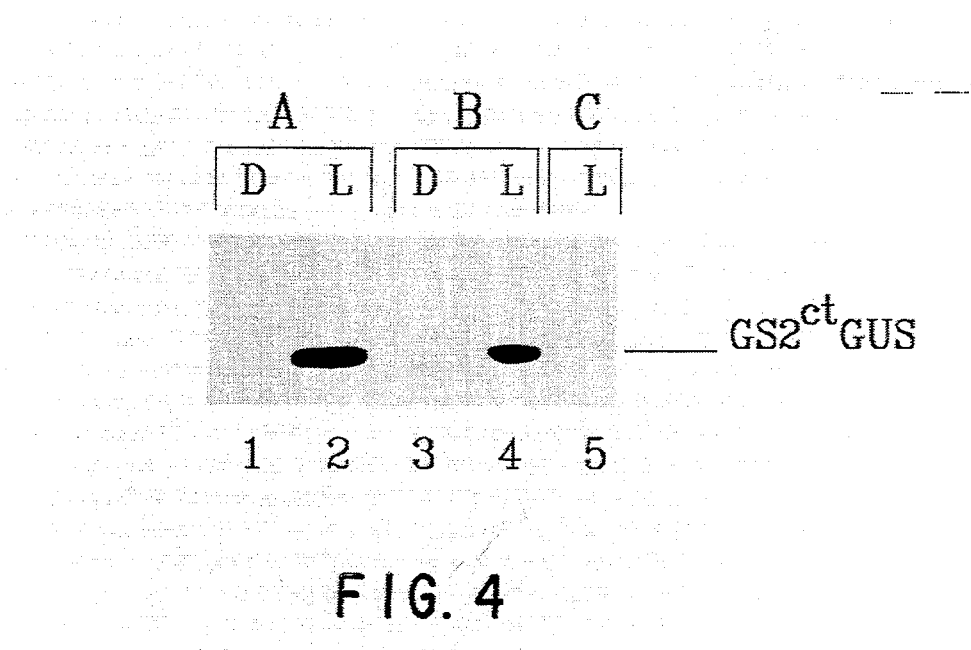

FIG. 4: Ribonuclease T2 protection analysis of pGS2$^{ct}$-GUS transcripts in light- vs. dark-grown transgenic tobacco. Autoradiograph of the 162 nt fragment protected from RNAse T2 digestion in hybridizations containing 50 µg of total RNA isolated from: A) and B) two separate pGS2$^{ct}$-GUS transformants; C) and a control, pBI101 transformant which was dark-adapted for 4 days (lanes 1 and 3), and subsequently grown in continuous white light for 24 hrs. (lanes 2, 4, and 5).

FIG. 5A: Nucleotide sequence of GS2 (SEQ. ID. NO. 1); FIG. 5B: Nucleotide sequence of GS3A (SEQ. ID. NO. 2); The sequence of the GS3A promoter is shown from nucleotide −1832 relative to the start of transcription to the BglII site extending to +107 (SEQ. ID. NO. 2, numbers 1 to 1939). Putative CAAT and TATA boxes are underlined, as is the first coding sequence ATG. The start of transcription was mapped to the two adenosines also underlined; the second of these is notated elsewhere as +1, and is written in lower case in the figure. Nucleotides −122 to −106 represent fragment a206 and the smallest defined sequence to bind the protein GS3A-F1 (SEQ. ID. NO. 2, numbers 1711 to 1727) FIG. 5C: Nucleotide sequence of GS3B (SEQ. ID. NO. 3).

Figure 6A:
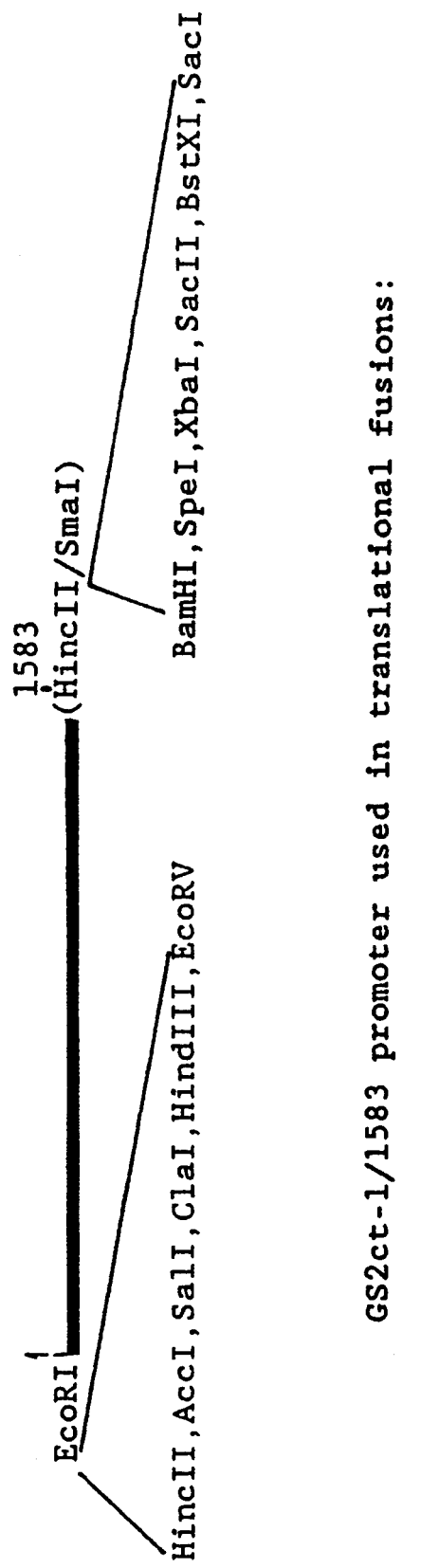
Figure 6B:
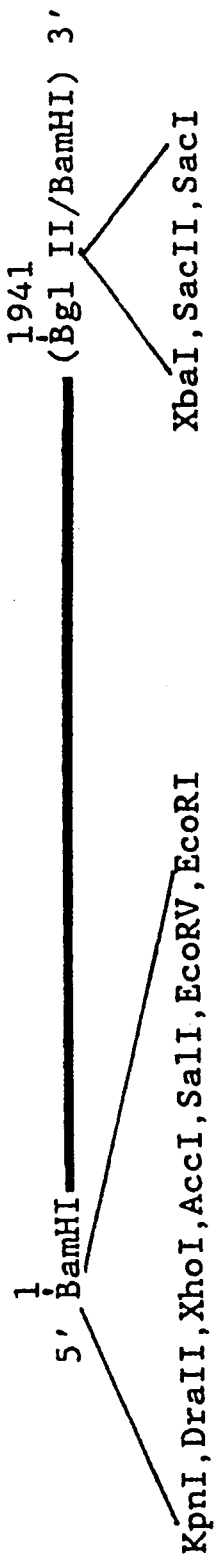
Figure 1:
Figures 2, 6B:
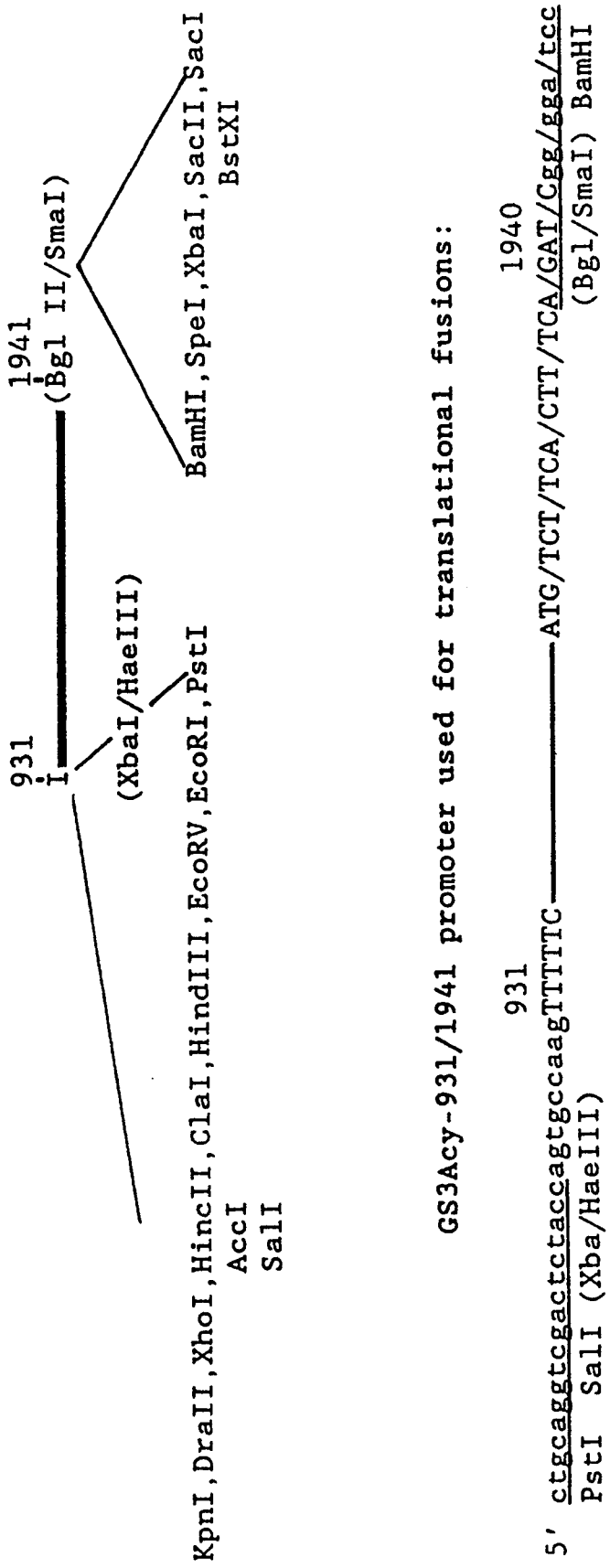

FIG. 6A: Promoter for GS2. FIG. 6B: Promoter for GS3A. FIG. 6C: Promoter for GS3B. For FIGS. 6A, 6B and 6C, gene sequences are in upper case letters, vector and linker sequences are in lower case letters. Restriction sites destroyed in cloning are marked in parentheses. All restriction sites are underlined. Numbers refer to the nucleotides of GS promoter as specified in FIGS. 5A, 5B, and 5C.

Figure 7:
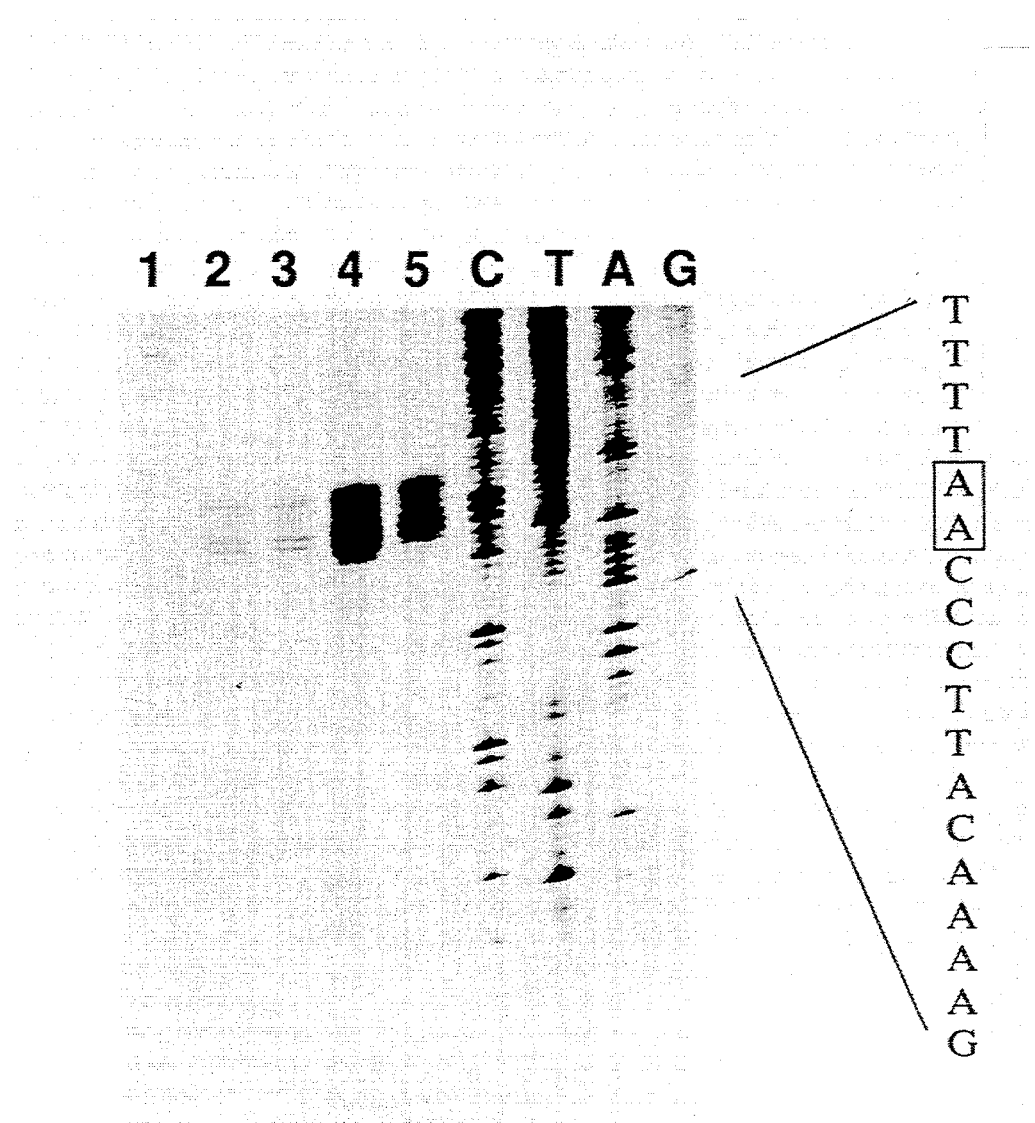

FIG. 7: Identification of the transcriptional start site of the GS3A promoter. 5' S1 nuclease analysis was undertaken on 10 µg of total RNA from leaves, roots, nodules and cotyledons. Oligonucleotide EW1 was used to prepare a labelled probe complementary to the GS3A mRNAs and also sequencing reactions on the non-coding strand. Lane 1: tRNA control; lane 2: leaf RNA; lane 3: root RNA; lane 4: nodule RNA; lane 5: cotyledon RNA. GATC are the sequencing reactions transcribed to the sense strand. The sequence from either side of the start site is shown with the two major transcriptional start sites boxed.

Figure 8:
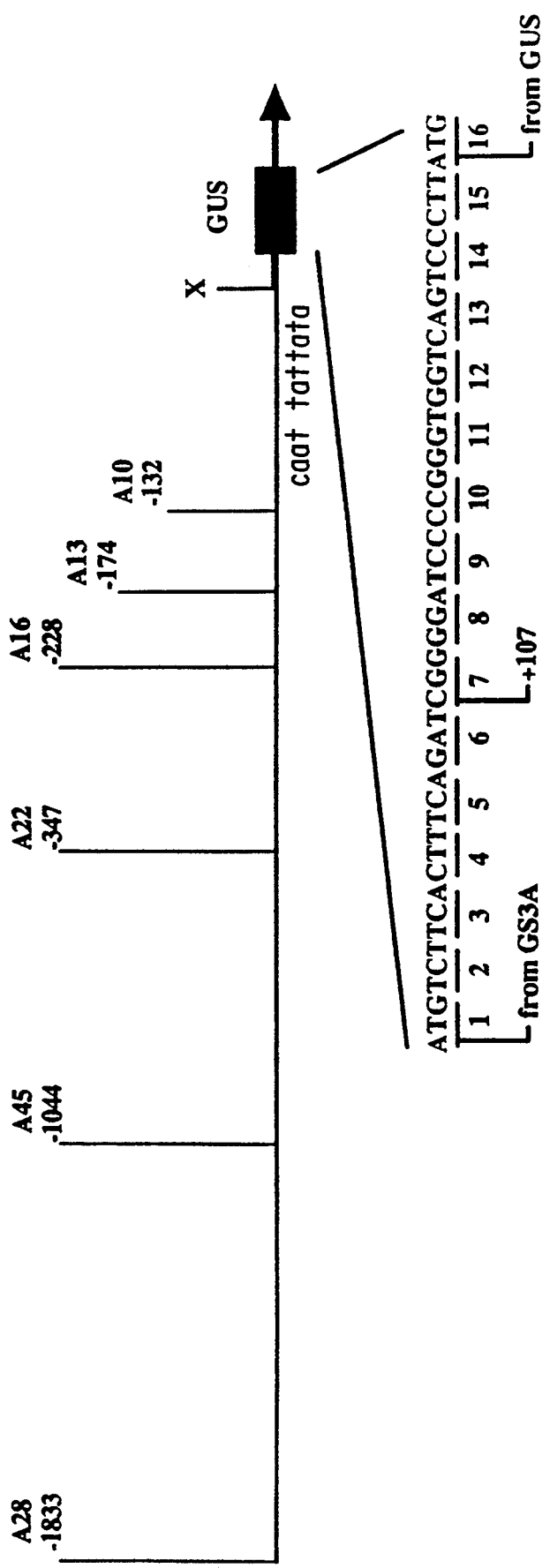
Figure 9A:
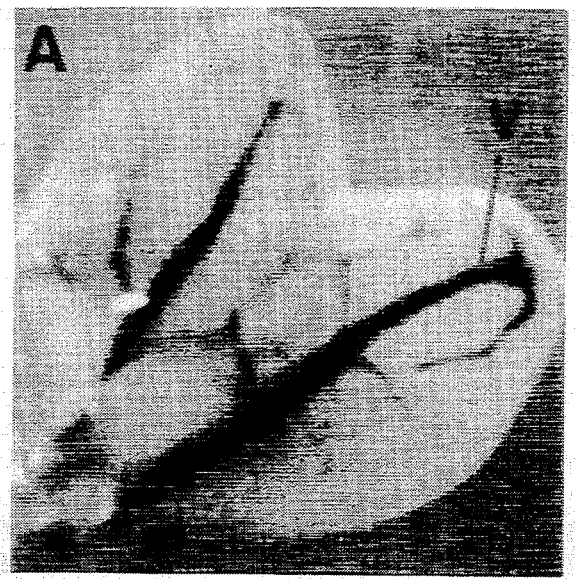
Figure 9B:
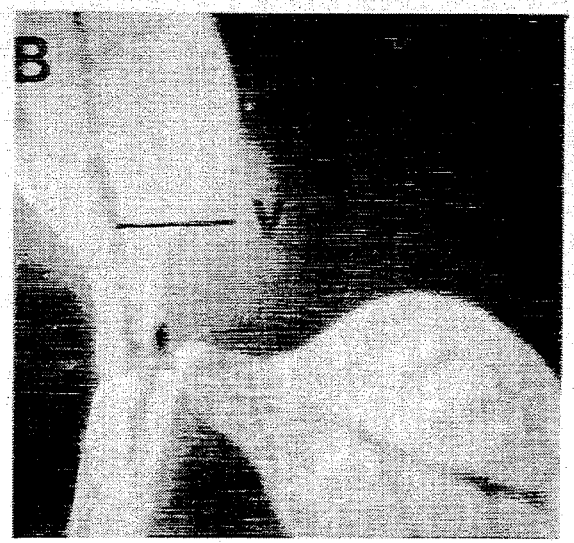
Figure 9C:
Figure 9D:
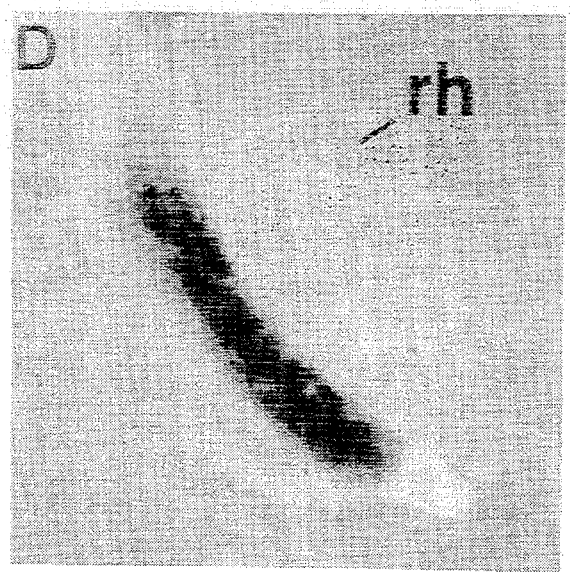
Figure 9F:
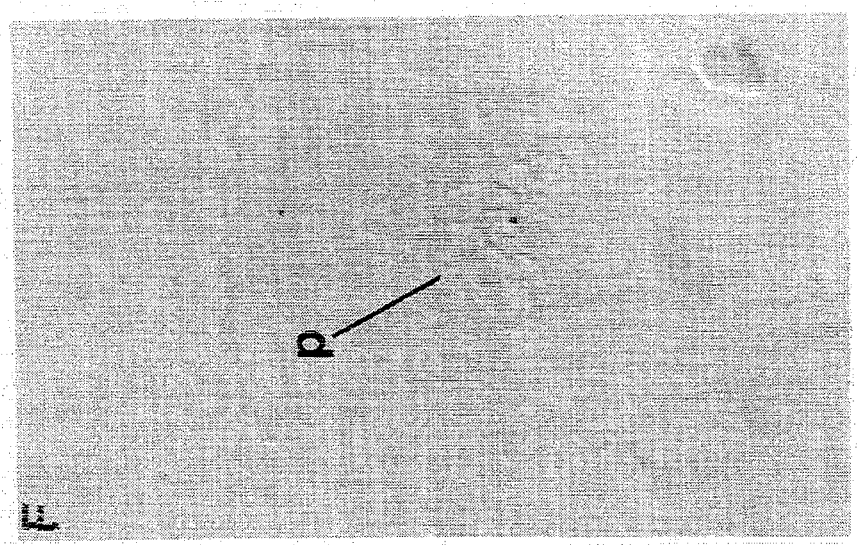
Figure 9E:
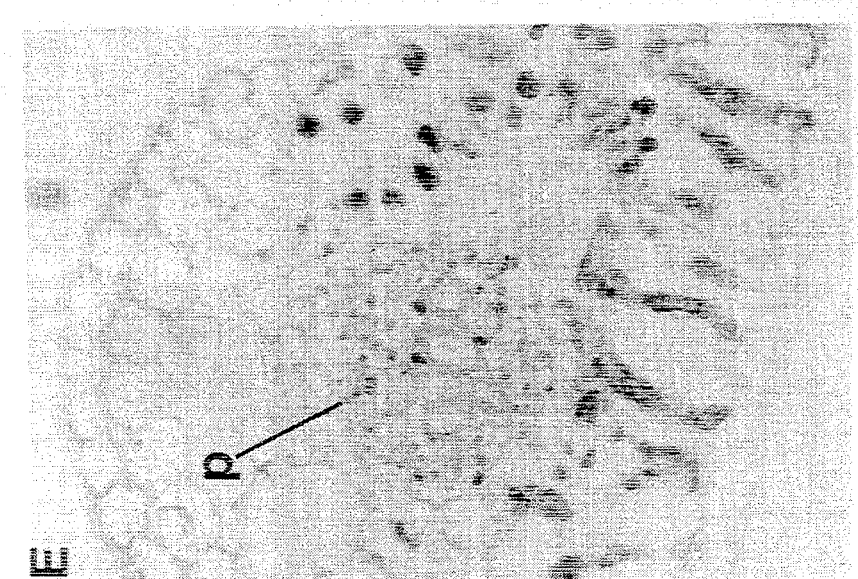

FIG. 8: Deletion analysis of the GS3A promoter. Six promoter deletions were transferred to transgenic tobacco and alfalfa in translational fusion to GUS. The relative positions of CAAT and TATA boxes and the transcriptional start site (X) are indicated schematically (exact positions for these can be found in FIG. 5B). The sequence of the first 16 codons illustrate the nature of the fusion constructed. Codons 1 to 6 are derived from GS3A coding sequence, codons 7 to 11 are derived from polylinker sequence, codons 12 to 15 are derived from the GUS leader, and codon 16 is the 5US ATG.

FIG. 9: Histochemical detection of GUS in transgenic tobacco. GUS expression in tobacco seedlings. Panels A and B: cotyledons of transgenic constructions A28 and A10, which correspond to the longest and shortest deletions respectively. Panel C: A28 seedlings. Panel D: root tip of an A28 seedling. Panels E and F: 8 µm leaf sections of a mature A28 alfalfa transformant (panel E is counterstained with erythrosin) showing expression localized to phloem. v: vasculature; rh: root hairs.

Figure 10A:
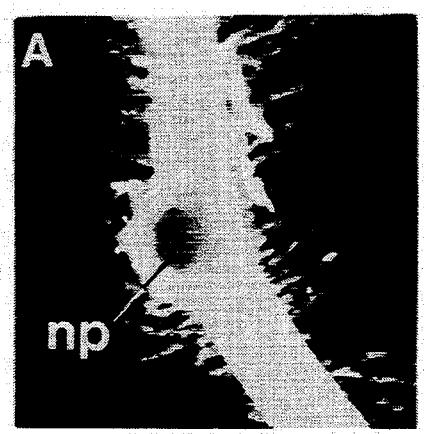
Figure 10B:
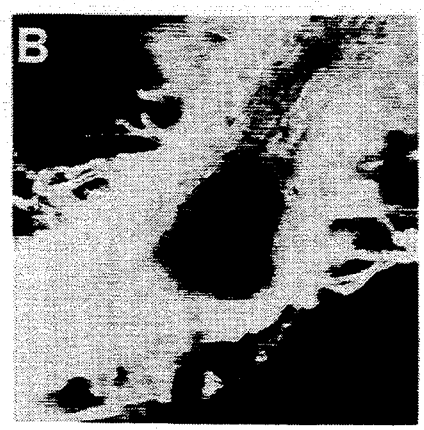
Figure 10C:
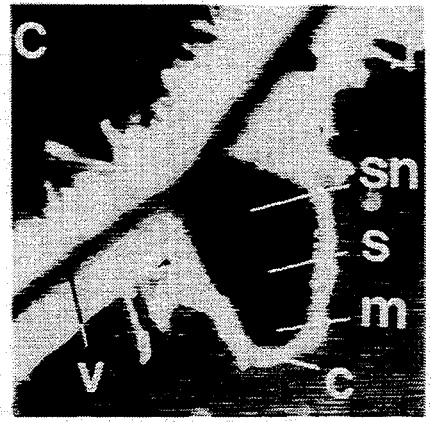
Figure 10D:
Figure 10E:
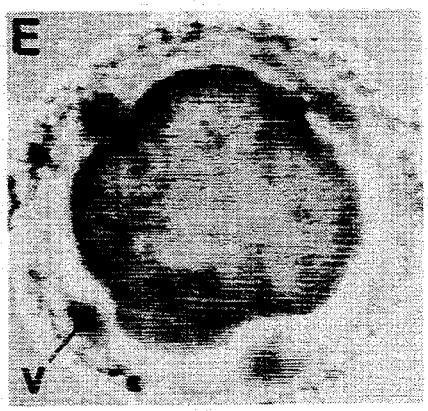
Figure 10F:
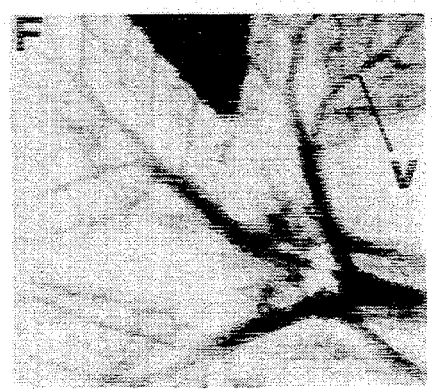
Figure 10G:
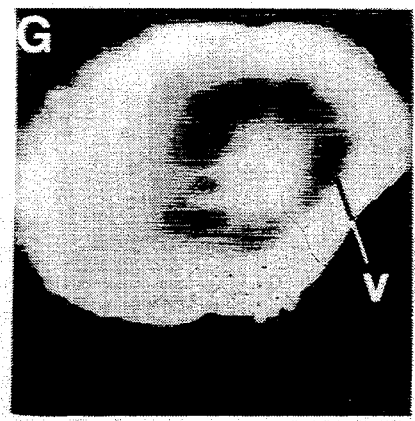
Figure 10H:
Figure 10:
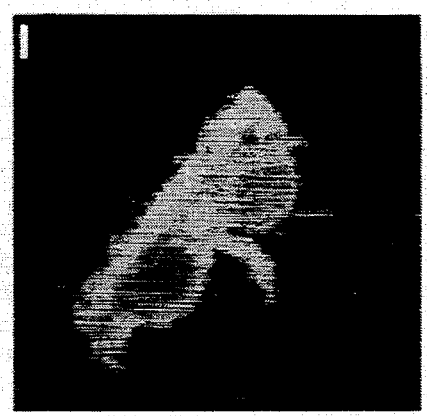
Figure 10:
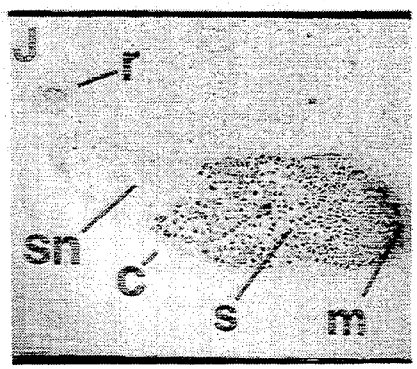
Figure 10K:
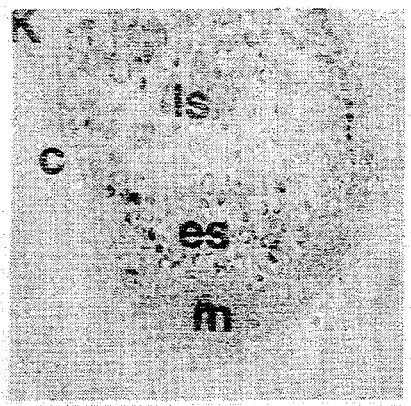
Figure 10L:
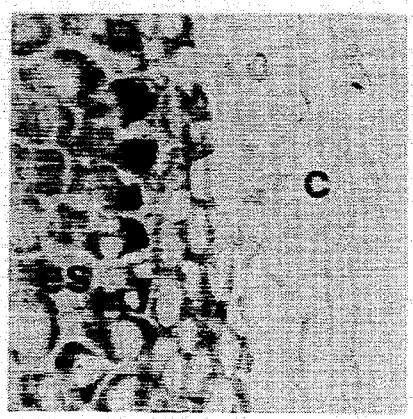

FIG. 10: Histochemical detection of GUS in transgenic alfalfa. Panels A to D: GUS expression in nodules of an A13 transformant at different stages of maturity (from between 2 and 5 weeks post-nodulation). Panel E: transverse section through an A13 nodule expressing GUS. Panel F: GUS expression in an A13 leaf. Panel G: transverse stem section, A13 transformant. Panel H: GUS expression in A28 nodules. Panel I: nodules on the pBI101 transformed control. Panels J, K, and L: 8 µm nodule sections (counterstained with erythrosin) allowing the definition of the cell-type expression of GUS (A28 transformants). np: nodule primordium; v: vasculature; c: cortical cells; m: meristematic cells; s: symbiotic zone; es: early symbiotic zone; ls: late symbiotic zone; sn: senescent zone; r: root.

Figure 11A:
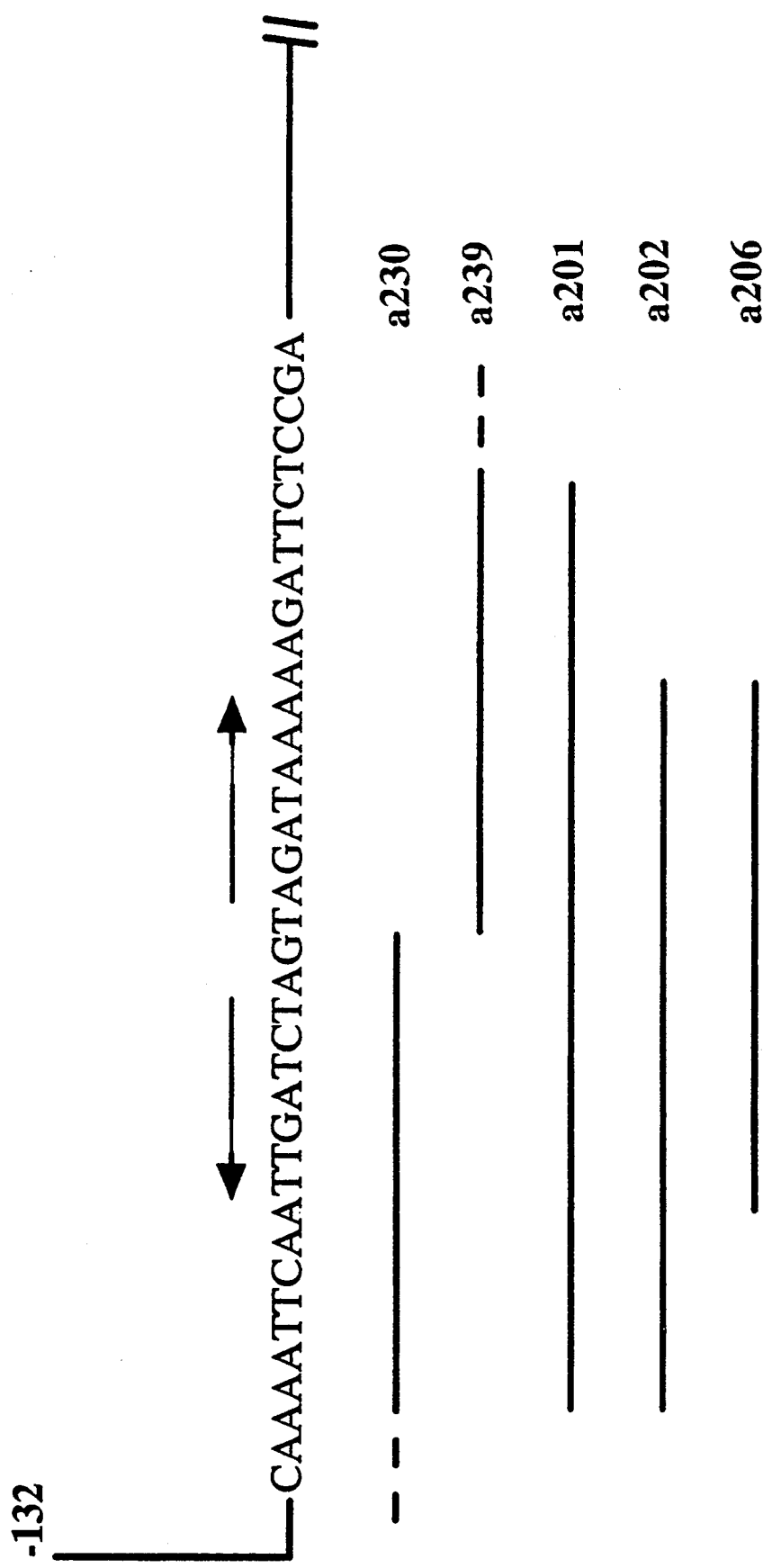
Figure 11B:
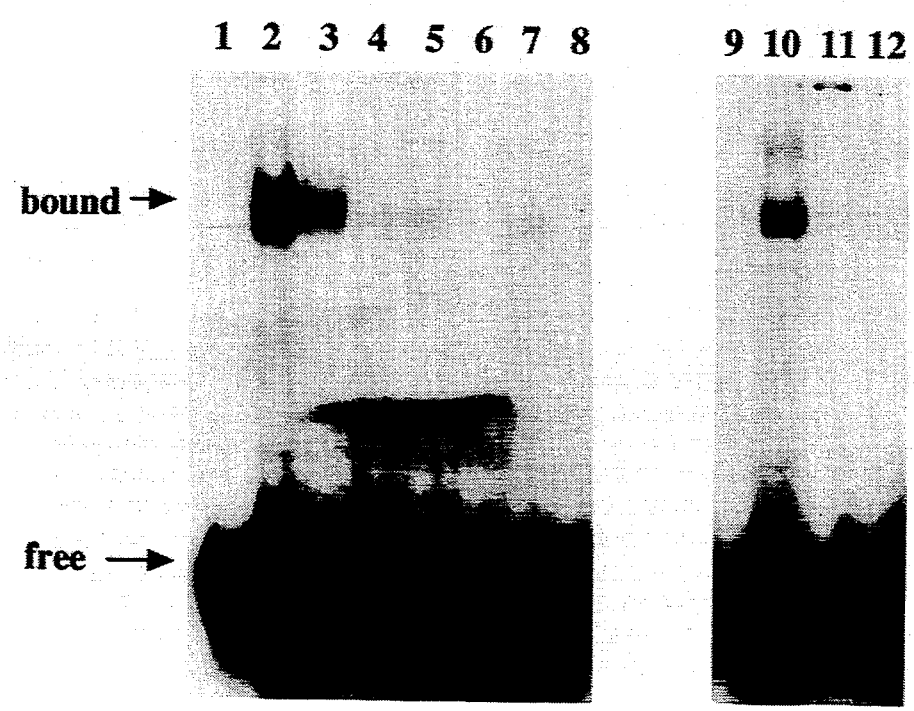
Figure 11C:
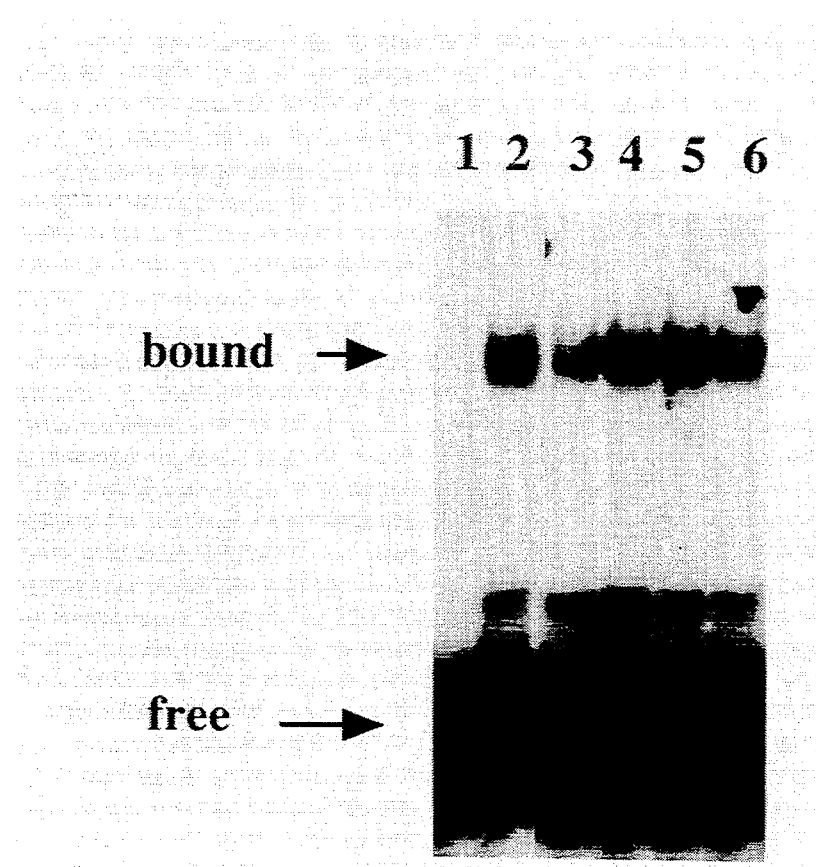

FIGS. 11A, 11B, and 11C: A putative cis-element in the GS3A promoter. FIG. 11A: The GS3A promoter sequence immediately adjacent to the shortest 5' deletion (A10) extending from −132 to −94 is shown (SEQ. ID. NO. 2, numbers 1701 to 1739). The imperfect palindrome contained in this sequence is indicated by the arrows. Bars below the DNA sequence indicate the five DNA fragments spanning this region of the GS3A promoter which were used in mobility-shift assays: a201 (−129 to −97; SEQ. ID. NO. 2, number 1704 to 1736); a202 (−129 to −106; SEQ. ID. NO. 2, number 1704 to 1727); a206 (−122 to −106; SEQ. ID. NO. 2 number 1711 to 1727); a230 (−173 to −114; SEQ. ID. NO. 2, number 1660 to 1719); a239 (−113 to −54; SEQ. ID. NO. 2, number 1720 to 1779). The dashed lines on fragment a230 and a239 indicate that these fragments extend laterally beyond the sequence shown to the positions indicated above. Nuclear extracts used in these assays were prepared from mature, dark-adapted tobacco plants. FIG. 11B: Fragement a202 (lanes 1–8), and fragment a206 (lanes 9–12) were used as probes in gel-mobility assays using tobacco nuclear extracts. All lanes are from the same gel. Lane 1: free a202 probe; lane 2: probe+extract; lane 3: probe+extract+10-fold molar excess of unlabelled a202; lane 4: probe+extract+50-fold molar excess of unlabelled a202; lane 5: probe+extract+10-fold molar excess of unlabelled a230; lane 6: probe+extract+50-fold molar excess of unlabelled a230; lane 7: probe+extract+10-fold molar excess of unlabelled a239; lane 8: probe+extract+50-fold molar excess of unlabelled a239. Lane 9: free a206 probe; lane 10: probe+extract; lane 11: probe+extract+10-fold molar excess of unlabelled a206; lane 12: probe+extract+50-fold molar excess of unlabelled a206. Lane 13: probe+extract+10-fold molar excess of a202 competitor; lane 14: probe+extract+50-fold molar excess of a202 competitor. FIG. 11C: Fragment a201 was used as a probe in DNA mobility-shift assays again using tobacco nuclear extracts. All lanes are from the same gel. Lane 1: free a201 probe; lane 2: probe+extract; lane 3: probe+extract+25-fold molar excess of a GT1-binding tetrameric competitor; lane 4: probe+extract+125-fold molar excess of the same competitor; lane 5: probe+extract+25-fold molar excess of a mutant tetrameric competitor which does not bind GT1; lane 6: 125-fold molar excess of the same mutant competitor. In each case approximately 1 ng of probe was used corresponding to c. 10,000 counts per minute.

5. DETAILED DESCRIPTION OF THE INVENTION

The present invention relates to novel plant organ-specific transcriptional promoters which control the expression of glutamine synthetase isoenzymes, and provides for (i) promoter elements such as GS2, GS3A and GS3B, which have nucleotide sequences substantially as depicted in FIGS. 5A, 5B and 5C, respectively (SEQ. ID. NOS. 1, 2 and 3, respectively), or nucleotide sequences homologous thereto; (ii) gene fusions containing these promoter elements; (iii) methods for producing tissue-specific expression of glutamine synthetase or heterologous proteins utilizing the novel promoters; and (iv) transgenic plants containing transgenes which include the promoter elements of the invention. The invention is based, in part, on the discovery that the promoters for chloroplast GS2 and cytosolic GS3 of *Pisum sativum* confer non-overlapping, cell-specific expression patterns to the beta-glucuronidase (GUS) reporter gene in transgenic tobacco plants (See Section 6, infra). The promoter for chloroplast GS2 was observed to direct GUS expression within photosynthetic cell types (e.g. palisade parenchymal cells of the leaf blade, chlorenchymal cells of the midrib and stem, and in photosynthetic cells of tobacco cotyledons). The promoter for chloroplast GS2 appeared to retain the ability to confer light-regulated gene expression in the heterologous transgenic tobacco system in a manner analogous to the light-regulated expression of the cognate gene for chloroplast GS2 in pea. These expression patterns may reflect the physiological role of the chloroplast GS2 isoform in the assimilation of ammonia generated by nitrite reduction and photorespiration. In contrast, the promoter for cytosolic GS3A was found to direct expression of GUS specifically within the phloem elements in all organs of mature plants. This phloem-specific expression pattern suggests that the cytosolic GS3A isoenzyme may function to generate glutamine for intercellular nitrogen transport. In germinating seedlings, the intense expression of the cytosolic GS3A&cy;-GUS transgene in the vasculature of cotyledons suggests a role for cytosolic GS3A in the mobilization of nitrogen from seed storage reserves.

For purposes of clarity of disclosure, and not by way of limitation, the invention is described in the following subsections:

(i) Identification of promoter elements associated with glutamine synthetase genes;
(ii) Novel glutamine synthetase promoter elements;
(iii) Gene fusions containing glutamine synthetase promoter elements; and
(iv) Creation of transgenic plants containing recombinant glutamine synthetase promoter elements;
(v) Utility of the GS promoter elements.

5.1. Identification of Promoter Elements Associated with Glutamine Synthetase Genes According to the present invention, promoter elements associated with glutamine synthetase genes may be identified from any species of plant, bacteria, or virus using any method known in the art. For example, genomic DNA libraries may be screened for clones containing sequences homologous to known glutamine synthetase genes or, alternatively, glutamine synthetase promoter sequences. For example, cDNA clones corresponding to mRNA which encodes glutamine synthetase, or oligonucleotide probes corresponding to known glutamine synthetase amino acid sequence may be used to identify homologous clones in a genomic DNA library using methods such as, for example, the method set forth in Benton and Davis (1977, Science 196:180) for bacteriophage libraries, and Grunstein and Hogness (1975, Proc. Natl. Acad. Sci. U.S.A. 72:3961–3965) for plasmid libraries. Retrieved clones may then be analyzed by restriction-fragment mapping and sequencing techniques according to methods well known in the art.

In another approach, nucleotide sequences of GS2, GS3A or GS3B promoters described herein (FIGS. 5A, 5B and 5C, respectively; SEQ. ID. NOS. 1, 2 and 3, respectively), portions thereof or nucleotide sequences homologous thereto may be used to screen genomic libraries to identify genomic clones containing homologous promoter elements using the standard techniques described supra. For example, the plasmids described in FIGS. 6A, 6B, and 6C or the fragments described in FIG. 8 and FIGS. 11A and 11B could be used to such ends.

Alternatively, oligonucleotides derived from the GS2, GS3A and GS3B promoter sequences described herein could be used as primers in PCR (polymerase chain reactions) to generate GS promoter sequences from any species. For a review of such PCR techniques, see for example, Gelfand, 1989, PCR Technology. Principles and Applications for DNA Amplification, Ed., H. A. Erlich, Stockton Press, N.Y., and Current Protocols in Molecular Biology, "Vol. 2 Ch 15 Eds. Ausubel et al., John Wiley & Sons, 1988.

Using any of the foregoing approaches, homologous glutamine synthetase promoters in pea or in other species of plant, bacteria, or other organism may be identified.

5.2. Novel Glutamine Synthetase Promoter Elements

FIGS. 5A, 5B or 5C sets forth the nucleotide sequences of the GS2 (FIG. 5A; SEQ. ID. NO. 1), GS3A (FIG. 5B; SEQ. ID. NO.2), and GS3B (FIG. 5C; SEQ. ID. NO. 3) promoter elements. The activity of the GS2 promoter is induced by light. When engineered into transgenic plants, GS2 directs transgene expression predominantly within photosynthetically active cells, the palisade and spongy parenchymal cells of the leaf blade, in collenchymal and chlorenchymal cells of the stem and in photosynthetic cotyledons. In contrast, the GS3 promoters confer vasculature-specific expression in leaves, stems and roots of mature transgenic plants, and in the cotyledons and roots of developing seedlings.

By promoter deletion analysis, we defined the region of the GS3A promoter involved in its phloem-specific and developmentally-regulated expression. A short DNA element indicated in FIG. 5B from nucleotide residue number −132 to number +107 (SEQ. ID. NO. 2 from nucleotide number 1701 to 1939) is functional when engineered into transgenic plants, and is qualitatively equivalent to the full-length GS3A promoter in its expression. This DNA element comprises three portions: (a) the GS3A promoter element (FIG. 5B, nucleotide residue numbers −132 to −1; SEQ. ID. NO. 2 from nucleotide number 1701 to 1832); (b) the 5′ non-translated leader sequence for the GS3A structural gene (FIG. 5B, nucleotide residue numbers 1 to 88; SEQ. ID. NO. 2 from nucleotide number 1833 to 1920); and (c) the first six codons of the GS3A structural gene (FIG. 5B, nucleotide residue numbers 89 to 107; SEQ. ID. NO. 2, from nucleotide number 1921 to 1939).

DNA fragments a201 (FIG. 5B, nucleotide numbers −129 to −97; SEQ. ID. NO. 2, nucleotide numbers 1704 to 1832), a202 (FIG. 5B, nucleotide numbers −129 to −106; SEQ. ID. NO. 2, nucleotide numbers 1704 to 1727) and a206 (FIG. 5B, nucleotide numbers −122 to −106; SEQ. ID. NO. 2, nucleotide numbers 1711 to 1727) contained within the −132 GS3A promoter element (shown in FIG. 11A) bind to a proteinaceous factor, GS3A-F1, found in whole-cell extracts of pea, and nuclear extracts of pea and tobacco (see Section 7.2.3., infra). Nuclear and whole cell plant extracts were analyzed by DNA mobility-shift techniques to identify this novel protein which bound to a 17 bp DNA element contained within the −132 GS3A promoter element (FIG. 5B from nucleotide residue number −122 to −106; SEQ. ID. NO. 2 nucleotide numbers 1711 to 1727), having the following sequence: TTGATCTAG-TAGATAAA.

The present invention provides for recombinant DNA constructs which contain nucleotide sequences substantially as depicted in FIGS. 5A, 5B, or 5C (SEQ. ID. NOS. 1, 2 or 3, respectively), functional portions thereof, and nucleotide sequences homologous thereto. Functional portions of the glutamine synthetase promoters described herein refers to regions of the nucleic acid sequence which are capable of promoting transcription under a specific set of conditions, in a particular cell type, or otherwise. Such functional portions include but are not limited to the −132 bp element of the GS3A promoter (supra); the a201, a202 and a206 sequences contained within the −132 GS3A promoter element (supra); and fragments which similarly display functional activity for GS2 or GS3B. Nucleotide sequences homologous to the glutamine synthetase promoters described herein refers to nucleic acid sequences which are capable of hybridizing to the nucleic acid sequences depicted in FIGS. 5A, 5B, or 5C (SEQ. ID. NOS. 1, 2 or 3) in standard hybridization assays or are homologous by sequence analysis (containing a span of 10 or more nucleotides in which at least 50 percent of the nucleotides are identical to the sequences presented herein). Homologous nucleotide sequences refer to nucleotide sequences including, but not limited to, glutamine synthetase promoter elements in diverse plant species as well as genetically engineered derivatives of the promoter elements described herein. According to the latter embodiment, it may be found that altering the sequence of the promoter element may result in a change in promoter activity, such as an increase or decrease in promoter strength or a different pattern of cell or organ-specific expression. Such engineered promoter elements may be used, according to the invention, to design optimal gene fusion systems for a variety of applications.

5.3. Gene Fusions Containing Glutamine Synthetase Promoter Elements

The glutamine synthetase promoter elements of the invention may be used to direct the expression of glutamine synthetase or any other protein, referred to as a heterologous protein or as a desired protein, or the expression of an RNA product, including, but not limited to, an "antisense" RNA. For example, recombinant constructs containing a glutamine synthetase promoter element as defined in Sections 5.1 and 5.2 supra and a nucleic acid sequence encoding a desired protein are within the scope of the present invention. Such constructs may include the entire GS promoter sequence, or functional portions as described in Section 5.2, ligated to the coding sequence of interest, and may or may not include sequences that encode amino acids of the glutamine synthetase structural gene. The constructs should be designed so that the nucleic acid encoding the desired protein is in phase with contiguous sequences of GS such that translation will result in an amino acid sequence which correlates with the amino acid sequence of the native form of the desired protein.

In various embodiments of the invention, it may be desirable to include additional nucleotide sequences in the glutamine synthetase promoter recombinant constructs. Such additional nucleotide sequences may include but are not limited to, sequences encoding a ribosome binding site; sequences encoding 5′ untranslated leader sequences of mRNA species, including but not limited to the 5′ non-translated leader of GS3A (see FIG. 5B, nucleotide residue numbers 1-88; SEQ. ID. NO. 2 nucleotide number 1834 to 1920) which may confer or enhance phloem-specific expression; an intron; a 3′ non-translated sequence, such as a polyadenylation signal; sequences encoding an initiation codon or a signal peptide (which facilitates secretion of the desired protein); and targeting peptides, such as peptides which target the desired protein to chloroplasts or to the cell nucleus. In preferred embodiments of the invention which utilize the *Agrobacterium tumefaciens* system for plant transformation, the recombinant construct of the invention may additionally contain the left and right T-DNA border sequences.

In addition, the recombinant constructs of the invention may include a selectable marker for propagation of the constructs. For example, if the construct is to be propagated in bacteria, it may comprise a gene for antibiotic resistance. Suitable vectors for propagating the construct would include plasmids, cosmids, and viruses, to name but a few.

5.4. Creation of Transgenic Plants Containing Recombinant Glutamine Synthetase Promoter Elements The recombinant constructs containing a gene of interest placed under the control of the GS promoter elements described herein may be used to transform cells in culture or to engineer transgenic plants, so that expression of the gene of interest, or transgene is driven by the GS promoter element. In preferred embodiments of the invention, the *Agrobacterium tumefaciens* gene transfer system may be used to introduce the recombinant constructs of the invention into plants; generally, this system may be utilized to transfer DNA into dicotyledonous plants (Bevan et al., 1982, Ann. Rev. Genet. 16:357-384; Rogers et al., 1986, Methods Enzymol. 118:627-641; Fraley et al., 1986, CRC Crit. Rev. Plant Sci. 4:1-46; Hooykaas et al., 1984, Adv. Genet. 22:210-283; Nester et al., 1984, Ann. Rev. Plant Physiol. 35:387-413). To this purpose, vectors such as, but not limited to, binary Agrobacterium vectors for plant transformation may be utilized, such as, for example, the vector described by Bevan (1984, Nucl. Acids Res. 12:8711-8721). Xanthi may be transformed by a leaf inoculation procedure such as that described by Horsch et al. (1985, Science 227:1229-1231).

Additional methods for introducing DNA into plants may also be utilized, particularly if the recombinant construct is to be used to create a transgenic monocotyledonous plant. Such methods would include, but are not limited to polyethylene glycol) and calcium-mediated uptake of naked DNA (Hain et al., 1985, Mol. Gen. Genet. 199:161-168; Paszkowski et al., 1984, EMBO J. 3:2717-2722; Potrykus et al., 1985, Mol. Gen. Genet. 199:169-177), electroporation (Fromm et al., 1985, Proc. Natl. Acad. Sci. U.S.A. 82:5824-5828), microinjection and cell gun.

In order to identify successful transformants, it may be desirable to transform host cells with a second construct which comprises a selectable marker or reporter gene. The second construct may be introduced separately or in tandem with the construct which comprises the glutamine synthetase promoter and the sequence encoding the desired gene product. If not constructed in tandem, the second construct may also comprise a glutamine synthetase promoter, such that expression of selectable marker or reporter gene function may serve as an indicator of promoter activity and thereby provide evidence that the gene encoding the desired gene product is actively transcribed. This may be useful when a desired protein may have activity which is difficult to identify (e.g. the desired protein influences crop yield). Selectable markers would include genes which engender antibiotic resistance (for example, kanamycin resistance) or which encode a reporter gene, including but not limited to the gene for beta-glucuronidase (Jefferson, 1987, Plant Mol. Bio. Rep. 5:387-405), neomycin phosphotransferase (NPT II), and luciferase (Ow et al., 1986, Science 234:856-859) to name but a few. Detection of reporter gene expression may then be performed using methods known in the art.

Alternatively, transformants may be tested for the presence of recombinant construct by methods which would identify foreign DNA sequences, such as the Southern blot procedure. Transcription of recombinant constructs could be detected by isolating RNA from the transformant and screening for the expected transcript by Northern blot or RNA protection experiments (see Section 6.1.6., infra). Likewise, translation of the desired protein could be detected by protein gel electrophoresis, Western blot techniques, immunoprecipitation or enzyme-linked immunoassays.

Using similar techniques, the expression of the recombinant constructs of the invention may be detected in specific plant organs or tissues by determining the presence of RNA, protein, selectable marker, or reporter gene which may serve as an indicator of transcription resulting from recombinant glutamine synthetase promoter activity.

In specific embodiments of the invention, the GS2 promoter or GS2 homologous sequences may be detectably active in tissues such as photosynthetically active cells, including the palisade and spongy parenchymal cells of the leaf blade, in collenchymal and chlorenchymal cells of the stem, in photosynthetic cotyledons, and, at low levels, in root tips. Light-enhanced promoter activity may be detected. In a specific embodiment of the invention, tissue specific and light-enhanced activity of the GS2 promoter and its equivalents may be detected by the expression of the reporter gene beta-glucuronidase (Jefferson, 1987, Plant Mol. Biol. Rep. 5:387-405; see Section 6, infra).

In further embodiments of the invention, the GS3A or GS3B promoters or homologous sequences may be detectably active in vascular tissues such as leaves, stems, and roots of the mature plant, and in the cotyledons and roots of developing seedlings. In a specific embodiment of the invention, tissue specific activity of the GS3 promoters and their equivalents may be detected by the expression of the reporter gene beta-glucuronidase (Jefferson, 1987, Plant Mol. Biol. Rep. 5:387-405; see Section 6, infra).

5.5. Utility of the Invention

The present invention may be utilized to direct the expression of glutamine synthetase or heterologous proteins using novel plant organ specific promoter elements. According to specific embodiments of the invention, the GS2, GS3A, or GS3B promoter elements, functional portions thereof, or sequences homologous thereto, (as described supra) may be used to direct the expression of glutamine synthetase or heterologous gene products via recombinant nucleic acid constructs.

In particular embodiments of the invention, the novel promoter elements may be used to direct the expression of glutamine synthetase. Such embodiments may be useful in the engineering of plants which are genetically deficient in endogenous synthesis of glutamine synthetase or which may benefit from over production of glutamine synthetase, and may be used to introduce an isoenzyme of glutamine synthetase into a cellular compartment normally occupied by an alternate isoenzyme. Furthermore, engineered forms of the promoters of the invention which result in greater activity or altered tissue distribution of promoter function, may be used to alter expression patterns of glutamine synthetase. Manipulation of glutamine synthetase production may be advantageously used to confer herbicide resistance (see infra).

According to particular embodiments of the invention, the GS2 promoter and its functional or homologous equivalents may be used to provide tissue specific and light enhanced expression of desired proteins or gene products (e.g., antisense RNA). The GS2 promoter is selectively active in photosynthetic tissues. The tissue selectivity of the GS2-like promoters may be utilized to express desired proteins or gene products in photosynthetic tissues. The gene products may impact on the physiology of the plant (i.e., alter the size, growth rate, or density of photosynthetic tissues) or may introduce a molecule which does not naturally occur in the tissue, such as an insect repellant or fungus-retardant agent. The fact that GS2 promoter activity is enhanced by light provides the opportunity to control the onset, duration, and termination of expression of a desired gene product; this capability may be especially useful when a critical period of development of a plant or plant product exists and exposure to a gene product (e.g. a growth hormone expressed under the control of a GS2 promoter) may optimally be used to alter the properties of the plant or plant product.

According to further particular embodiments of the invention, the GS3 promoters and their functional or homologous equivalents may be used to provide phloem specific expression of desired proteins or gene products. Phloem specific expression of desired gene products may be used, for example, to alter plant metabolism; since plant nutrients (carbon and nitrogen-containing compounds) are transmitted via the phloem, expression of foreign genes specifically within the phloem could be used to increase the efficiency of nutrient uptake. In further embodiments of the invention, phloem-specific expression could be utilized in the mass production of foreign proteins (including, for example, lymphokines or antibody molecules) which could be recovered from the phloem exudate by "bleeding".

GS2 and GS3 promoter elements may be useful in imparting resistance to viral diseases to transgenic plants. Although viral infection in plants is not completely understood, it is believed that viruses move through plants either by short distance cell to cell spread (through plasmodesmata) or by dissemination over longer distances via the plant vascular system. It has been suggested that if a virus has a specific relationship to a plant tissue, it is most commonly associated with phloem tissue; both phloem-specific as well as nonrestricted viruses have been identified in the phloem (Esau, 1969, in "The Phloem," Gebruder Borntraeger, Berlin, pp. 252–262). A role for vital coat protein in preventing long-distance transport of virus has been observed in a variety of systems. Plants transformed to express tobacco mosaic virus protein were found to be resistant to tobacco mosaic virus infection; interestingly, efficient movement of virus through plant stem was found to be prevented by grafting a section of plant expressing viral coat protein into the movement path of the virus (Baulcombe and Hull, 1989, Nature 341:189). Tumer et al. (1987, EMBO J. 6:1181-1181) found that tobacco and tomato plants which expressed chimeric alfalfa mosaic virus (AlMV) coat protein were significantly delayed in symptom development after exposure to infectious AlMV, and some escaped infection altogether. Hemenway et al., (1989, in "Discoveries in Antisense Nucleic Acids" Brakel, ed., Gulf Publication Co., Houston, Tex., pp. 165–174) demonstrated protection against virus infection in transgenic plants expressing the viral coat protein or corresponding antisense RNA from tobacco mosaic virus, cucumber mosaic virus, and potato virus X. In specific embodiments of the invention, the GS2 and/or GS3 promoter elements may be used to express viral coat protein or the corresponding antisense mRNA in viral target tissues. Since viral spread appears to occur, at least in part, via the phloem, in a preferred embodiment a GS3 promoter element may be used to direct phloem-specific expression of a viral coat protein or its corresponding mRNA.

Furthermore, non-viral pathogens including mycoplasma-like organisms (MLO's) are also transmitted by phloem. MLO's cause a severe plant disease called "yellows" which devastates many citrus crops. GS3 phloem specific promoter may be used to express protein or nucleic acid which negatively affects MLO expression.

In still further embodiments of the invention, GS2 and GS3 promoter elements may be used to develop plants which are resistant to herbicides. Like viruses, many herbicides are transported through plants via phloem tissue. Furthermore, many of the newer, highly potent herbicides inhibit plant growth by interfering with the biosynthesis of essential amino acids rather than by inactivating a component of the photosynthetic apparatus (Shah et al., 198, in "Temporal and Spatial Regulation of Plant Genes", Verma and Goldberg, eds., Springer-Verlag, N.Y.); as a result, these new herbicides have a broad spectrum of activity which discriminates poorly between weeds and crops. Several of these herbicides are directed at glutamine synthetase activity and/or are directed toward enzyme expressed in chloroplasts.

For example, glyphosate (N-[phosphonomethyl]glycine) is a broad spectrum nonselective herbicide which inhibits 5-enolpyruvylshikimate-3-phosphate (EPSP) synthase, an enzyme normally localized in the chloroplast; overproduction Of unaltered or altered EPSP synthase, targeted to chloroplasts via a transit peptide, appeared to inhibit glyphosate toxicity (Shah et al., 1986, Science 233:478–481; Steinrucken and Amrhein, 1980, Biochem. Biophys. Res. Commun. 94:1207; Rubin et al., 1984, Plant Physiol. 75:839).

Phosphinothricin, a herbicide derived from a Streptomyces tripeptide antibiotic is structurally similar to glutamine and glutamate, and is a competitive inhibitor of glutamine synthetase (La Rossa and Falco, 1984, Trends in Biotechnology 2:158–161). Inhibition of phosphinothricin causes rapid accumulation of ammonia which is toxic to the plant (Tachibana et al., 1986, J. Pest. Sci. 11:33–37). A mutant of alfalfa tissue which overproduces glutamine synthetase has been observed to be resistant to the effects of the herbicide (Donn et al., 1984, J. Mol. Appl. Genet. 2:621–635). Similarly, a gene that encodes the detoxifying enzyme phosphinothricin acetyl transferase has been cloned; when expressed in calli, under the control of the camy 35S promoter, the calli are resistant to the herbicide.

Sulfonylurea herbicides inhibit the activity of acetolactate synthase (ALS), a nuclear-encoded chloroplast localized enzyme (Chaleff and Ray, 1984, Science 223:1148–1151; Jones et al., 1985, Plant Physiol. 77:S293). Mutations of the ALS gene which have resulted in resistance to sulfonylurea herbicides have been reported (Yadav et al., 1986, Proc. Natl. Acad. Sci. U.S.A. 83:4418–4422).

Resistance to atrazine (Cheung et al., 1988, Proc. Natl. Acad. Sci. U.S.A. 85:391–395), glyphosate (Comai et al., 1985, Nature 317:741–744), and sulfonylurea herbicides (Haughn et al., 1988, Mol. Gen. Genet. 211:266–271) have been achieved by the introduction of foreign genes encoding modified insensitive target proteins. Alternatively, resistance to phosphinotricin (De Block et al., 1987, EMBO J. 6:2513–2518) and bromoxynil (Stalker et al., 1988, Science 242:419–423) has been achieved by the expression of detoxifying enzymes. (See Streber and Willmitzer, 1989, Bio/Technology 7:811-815 for review).

In various embodiments of the invention, the GS2 and/or GS3 promoters may be used to achieve herbicide resistance in the herbicide target tissues. Thus, GS3 promoters may be used to achieve glutamine synthetase overproduction or the expression of inhibitory substrate or detoxifying enzyme in the phloem, the avenue of transport for most herbicides. Similarly, G2S promoters may be used to direct the expression of glutamine synthetase, inhibitory substrate or detoxifying enzyme in photosynthetic tissue; in specific embodiments, the glutamine synthetase, inhibitory substrate or detoxifying enzyme may be targeted to the chloroplasts via a transit peptide when herbicides are toxic to a chloroplast enzyme. The use of the GS2 and GS3 promoters of the invention focuses anti-herbicide activity to the tissue compartment most affected by herbicide instead of altering the physiology of the entire plant. For example, overproduction of glutamine synthetase throughout a plant may result in aberrancies of nitrogen metabolism, whereas overproduction in one tissue compartment would not. Furthermore, it may be possible to inhibit herbicide action using a mutant form of glutamine synthetase or an isoenzyme not normally found in a particular compartment, thereby minimizing the interference with endogenous isozyme activity.

6. EXAMPLE: IDENTIFICATION OF MESOPHYLL-SPECIFIC AND PHLOEM-SPECIFIC PROMOTER ELEMENTS

6.1. Materials and Methods

6.1.1. Isolation of Glutamine Synthetase Genomic Clones

Genomic clones encoding chloroplast or cytosolic GS of pea were isolated from a genomic library of *Pisum sativum* cv. "Sparkle" (Rogers Brothers Seed Co., Twin Falls, Id.) constructed in "Lambda Dash" (Stratagene, La Jolla, Calif.). Complete sequence analysis of each genomic clone revealed that the genomic clone for chloroplast GS2 (GS2$^{ct}$) corresponds to the GS185 cDNA (Tingey et al., 1988, J. Bio. Chem. 263:9651-9657), while the genomic clone for cytosolic GS (GS3A$^{cy}$) corresponds to the GS341 cDNA (Tingey et al., 1988, J. Bio. Chem. 263:9651-9657).

6.1.2. Construction of Plasmids and Transformation of Agrobacterium

A 1.5 kb EcoRI-HincII fragment of the promoter region of the pea nuclear gene for chloroplast GS2 (GS2$^{ct}$) was inserted into the polylinker of pBI101.2 (Jefferson, 1987, Plant Mol. Bio. Rep. 5:387-405) (Clontech, Palo Alto, Calif.) to create the plasmid, pGS2$^{ct}$-GUS (FIG. 1A). In addition to the promoter region of GS2, pGSct-GUS contains approximately 65 nt of the 5' untranslated leader of the GS2 mRNA and encodes 53 amino acids of the chloroplast transit peptide (Tingey et al., 1988, J. Bio. Chem. 263:9651-9657). The GS3A$^{cy}$-GUS fusion was constructed by inserting a 1.01 kb DNA fragment encompassing nucleotide position −903 to a BglII site at position +107 of the GS3A$^{cy}$ gene into the BamHI site upstream of the GUS gene in pBI101 (Jefferson, 1987, Plant Mol. Bio. Rep. 5:387-405). The GS3A$^{cy}$-GUS fusion gene was released from the plasmid as an XbaI-EcoRI fragment which was subsequently cloned into pMON505 (Horsch and Klee, 1986, Proc. Natl. Acad. Sci. USA. 83:4428-4432) to create the plasmid, pGS3A$^{cy}$-GUS (FIG. 1B). PGS3A$^{cy}$-GUS contains 88 nt of the 5' untranslated leader of GS3A mRNA and encodes six amino acids of the cytosolic GS protein (Tingey et al., 1988, J. Bio. Chem. 263:9651-9657).

6.1.3. Transformation and Growth of Transgenic Tobacco Plants

Binary vectors containing the GS-GUS constructs were transferred into the disarmed Agrobacterium stain LBA4404 by triparental mating as previously described (Bevan, 1984, Nucleic Acids Res. 12:8711-8721). *Nicotiana tabacum* cv. SR1 or *Nicotiana tabacum* cv. Xanthi was transformed by a leaf inoculation procedure (Horsch et al., 1985, Science 227:1229-1231). Regenerated shoots were selected for growth on medium containing kanamycin (200 μg/ml). Primary transformants were maintained in sterile culture and were also grown to maturity in soil. F1 seeds were sterilized in 10% sodium hypochlorite and germinated on MS medium containing 3% sucrose, 100 μg/ml kanamycin, and 500 μg/ml carbenicillin. Seedlings were grown in culture for several days at 26° C. in continuous white light.

6.1.4. Determination of Beta-Glucuronidase Expression

GUS enzyme assays and histochemical staining of mature plants were performed as previously described (Jefferson, 1987, Plant Mol. Bio. Rep. 5:387-405; Jefferson et al., 1987, EMBO J. 6:3901-3907). The whole mount histochemical staining of seedlings was performed as previously described (Benfey et al., 1989, EMBO J. 8:2195-2202). After incubation with the GUS substrate, 5-bromo-4-chloro-3-indolyl-B-D-glucuronic acid (Clontech, Palo Alto, Calif.), cross sections of mature plant organs and whole seedlings were cleared for chlorophyll by incubation with a solution of 5% formaldehyde, 5% acetic acid, and 20% ethanol for 10 minutes followed by 2 minute incubations with, respectively, 50% and 100% ethanol. Photomicrographs were taken with a Nikon Optiphot microscope using phase contrast optics.

6.1.5. Plant Growth Conditions for Light Induction Experiments

Transgenic plants containing the GS2$^{ct}$-GUS fusion gene were germinated and grown in soil in continuous white light for 4 weeks. The plants were transferred to black Lucite boxes within a dark environmental chamber for 4 days. Several leaves of each plant were collected in the dark and immediately frozen in liquid nitrogen. The plants were subsequently transferred to continuous white light for 24 hours and leaves were collected and frozen for RNA extraction.

6.1.6. Isolation of RNA and Ribonuclease Protection Assay

RNA was extracted from leaves of dark-adapted and light-grown transgenic tobacco plants using guanidine thiocyanate as a protein denaturant (Chirgwin et al., 1979, Biochem. 18:5294-5304). The DNA vector used (pJE1005) contained a 1.5 kb EcoRI-HincII fragment of the nuclear gene for chloroplast GS2 (GS2$^{ct}$) in the plasmid pTZ18U (US Biochemical, Cleveland, Ohio). A DNA template encompassing the 5' end of GS2$^{ct}$ was generated by HindIII digestion of pJE1005. The radioactive, antisense RNA probe for the RNAse protection assay was generated in vitro using T7 RNA polymerase (Melton, 1984, Nucleic Acid Res. 12:7035–7056). 50 μg of total RNA from transgenic tobacco plants was hybridized to an excess of the antisense RNA probe overnight in 80% formamide, 60 mM Pipes pH 6.4, 400 mM NaCl and 1 mM EDTA at 60° C. RNAse T2 digestions were performed in a volume of 390 μl containing 50 mM NaOAc pH 5.0, 100 mM NaCl, 2 mM EDTA, and 60 units/ml of RNAse T2 (Bethesda Research Labs.) (Costa et al., 1989, EMBO J. 8:23–29). Digestion products were separated on an 8% acrylamide/7M urea gel and exposed to X-Ray film at −80° C.

6.2. Results

6.2.1. Construction of GS-GUS Reporter Gene Fusions and Quantification of Beta-Glucuronidase Activity in Transgenic Plants Genomic clones encoding chloroplast or cytosolic GS of pea were isolated by hybridization to the corresponding cDNAs, pGS185 (Tingey et al., 1988, J. Bio. Chem. 263:9651–9657) and pGS341 (Tingey et al., 1988, J. Bio. Chem. 263:9651–9657), respectively. The genomic clone pGS2$^{ct}$ corresponds to the single nuclear gene for chloroplast GS2 (Tingey et al., 1988, J. Bio. Chem. 263:9651–9657). The genomic clone pGS3A$^{cy}$ corresponds to a gene for cytosolic GS (GS341) which encodes the predominant mRNA for cytosolic GS in a number of organs examined. Promoter elements from the gene for chloroplast GS2 and cytosolic GS3A were subcloned in translational fusions to the GUS reporter gene of pBI101.2 or pBI101, respectively, as described in Materials and Methods (Jefferson, 1987, Plant Mol. Bio. Rep. 5:387–405) to create pGS2$^{ct}$-GUS and pGS3A$^{cy}$-GUS (FIG. 1A and FIG. 1B). These chimeric genes were introduced into *Nicotiana tabacum* via Agrobacterium mediated plant transformation (Bevan, 1984, Nucleic Acids Res. 12:8711–8721).

GUS enzyme activity was measured in soluble protein extracts of leaves of 19 individual transgenic plants by a fluorimetric assay (Jefferson, 1987, Plant Mol. Bio. Rep. 5:387–405; Jefferson et al., 1987, EMBO J. 6:3901–3907) (Table I). GUS activity in leaves of primary transgenic plants containing the pGS2$^{ct}$-GUS construct averaged 46,984 pmol MU/mg protein/min, while GUS activity detected in the leaves of transgenic plants containing the pGS3A$^{cy}$-GUS chimeric construct was approximately 17-fold lower. The amount of GUS activity produced in transgenic plants containing pGS2$^{ct}$-GUS is comparable to that reported for other "strong" promoters such as that for the cauliflower mosaic virus 35S protein (Benfey et al., 1989, EMBO J. 8:2195–2202) and patatin (Rocha-Sosa et al., 1989, EMBO J. 8:23–29).

TABLE I

GUS Activity in Leaves of Transgenic Tobacco Plants
pmol MU/mg protein/min

| Chloroplast GS2$^{ct}$- GUS Transformants | | Cytosolic GS3A$^{cy}$- GUS Transformants | |
|---|---|---|---|
| pGS2$^{ct}$-GUS-1 | 13,070 | pGS3A$^{cy}$-GUS-1 | 2,183 |
| pGS2$^{ct}$-GUS-2 | 22,374 | pGS3A$^{cy}$-GUS-2 | 9,429 |
| pGS2$^{ct}$-GUS-3 | 53,155 | pGS3A$^{cy}$-GUS-3 | 1,940 |
| pGS2$^{ct}$-GUS-4 | 67,300 | pGS3A$^{cy}$-GUS-4 | 372 |
| pGS2$^{ct}$-GUS-5 | 60,373 | pGS3A$^{cy}$-GUS-5 | 648 |
| pGS2$^{ct}$-GUS-6 | 32,918 | pGS3A$^{cy}$-GUS-6 | 2,453 |
| pGS2$^{ct}$-GUS-7 | 43,084 | pGS3A$^{cy}$-GUS-7 | 1,740 |
| pGS2$^{ct}$-GUS-8 | 53,886 | | |
| pGS2$^{ct}$-GUS-9 | 40,802 | | |
| pGS2$^{ct}$-GUS-10 | 95,435 | | |
| pGS2$^{ct}$-GUS-11 | 43,568 | | |
| pGS2$^{ct}$-GUS-12 | 37,840 | | |

TABLE I-continued

GUS Activity in Leaves of Transgenic Tobacco Plants
pmol MU/mg protein/min

| Chloroplast GS2$^{ct}$- GUS Transformants | | Cytosolic GS3A$^{cy}$- GUS Transformants | |
|---|---|---|---|
| Average | 46,984 | Average | 2,681 |

*MU = Methylumbelliferone

Southern blot experiments using DNA from transgenic tobacco containing pGS2$^{ct}$-GUS or pGS3A$^{cy}$-GUS revealed that each transformed plant contained 1 or 2 copies of the transgene. The variation in the amount of GUS activity between individual transgenic plants was 7-fold for the pGS2$^{ct}$-GUS plants, and 25-fold for the pGS3A$^{cy}$-GUS plants (Table I). This degree of variation in GUS expression among individual transgenic plants is similar to that reported by others (Benfey et al., 1989, EMBO J. 8:2195–2202; Rocha-Sosa et al., 1989, EMBO J. 8:23–29), and is most likely the result of differences in positional insertion in the tobacco genome, or differences in the developmental stages of each plant used in this analysis.

6.2.2. The Promoter for Chloroplast GS2 Directs GUS Expression Specifically in Photosynthetic Cell Types In situ GUS assays were performed on sections of leaves, stems, and roots of mature transgenic tobacco plants FIGS. 2A, 2B, 2C, 2D, 2E, 2F, 2G and 2H and on whole tobacco seedlings (FIGS. 3A, 3B and 3C). These assays revealed that pGS2$^{ct}$-GUS or pGS3A$^{cy}$-GUS confer non-overlapping patterns of cell- and organ-specific expression on the GUS reporter gene in transgenic plants.

In situ staining of sections of the pGS2$^{ct}$-GUS transgenic plants reveals that the promoter for chloroplast GS2 directs high-level GUS expression in leaves, specifically in the parenchymal cells of the leaf blade (FIG. 2A). The most intense GUS staining occurs in the palisade parenchymal cells of the leaf blade which are specialized for photosynthesis and contain a large number of chloroplasts (FIG. 2B). In a cross section of the leaf midrib pGS2$^{ct}$-GUS activity is detected only in two photosynthetic cell layers (collenchyma and chlorenchyma), while the adjacent epidermal cell layer comprised of non-photosynthetic cells, shows no GUS expression (FIG. 2C). There is no GUS expression in the central vascular bundle of the midvein in the pGS2$^{ct}$-GUS plants (FIG. 2A). In cross sections of stem, GUS activity is detected in the photosynthetic chlorenchymal cells (FIG. 2D), while there is no GUS staining in the pith parenchymal, vascular, epidermal, or trichome cells of the stem (FIG. 2D). In roots, pGS2$^{ct}$-GUS is expressed at low levels in root tips where GS in plasmids functions in ammonia assimilation from the soil (Miflin, 1974, Plant Physiol. 54:550–555).

Figure 2F:
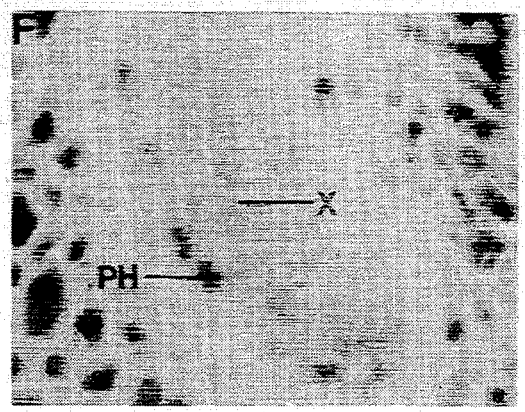
Figure 2G:
Figure 2H:
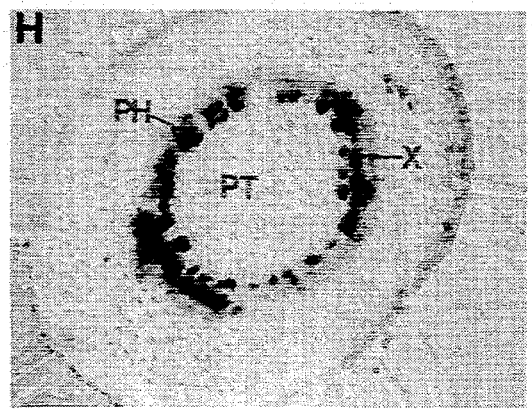

6.2.3. The Promotor for a Cytosolic GS Gene Directs GUS Expression Exclusively in Phloem Analysis of the pGS3$^{cy}$-GUS transgenic plants reveals that the promoter for cytosolic GS directs expression of GUS specifically within the vascular elements of leaves, stems, and roots of mature plants (FIG. 2E–2H). In leaves of pGS3$^{cy}$-GUS transgenic tobacco, histochemical staining for GUS occurs exclusively in the vasculature, in a punctate pattern indicative of phloem-specific expression (FIGS. 2E and 2F). In roots, the triarc staining pattern observed for pGS3$^{cy}$-GUS is also indicative of phloem-specific expression (FIG. 2G). This punctate pattern of GUS expression is also observed in a stem cross section where the internal phloem stains intensely (FIG. 2H).

6.2.4. Expression of the GS-GUS Fusions in Germinating Transgenic Tobacco Seedlings To examine the organ and cell-specific expression of pGS2$^{ct}$-GUS and pGS3$^{cy}$-GUS during plant development, GUS enzyme activity was detected in situ in whole mounts of germinating tobacco seedlings (Benfey et al., 1989, EMBO J. 8:2195-2202). This analysis reveals a striking contrast between the expression patterns conferred by the promoters for chloroplast GS2 and cytosolic GS3A (FIGS. 3A, 3B and 3C). In transgenic tobacco seedlings containing pGS2$^{ct}$-GUS, intense GUS staining is seen throughout the cotyledons, which are photosynthetic in tobacco (Avery, 1932, Am. J. Bot. 20:309-327) (FIG. 3A). In pea cotyledons, which are non-photosynthetic (Lovell (1977) in The Physiology of the Garden Pea, eds. Sutcliffe, J. & Pate, J. S. (Academic Press, London), pp. 265-290), there is low level expression of the mRNA for chloroplast GS2. Therefore, expression of chloroplast GS2 correlates with photosynthetic capacity rather than strict organ-type. In these same pGS2$^{ct}$-GUS seedlings, GUS activity is not detected in the hypocotyl (FIG. 3A), and is present at very low levels in the root tips (FIG. 3A).

For cytosolic GS, pGS3A$^{cy}$-GUS constructs are expressed exclusively in vasculature of developing transgenic seedlings (FIG. 3B). This vasculature-specific staining pattern is most intense in the cotyledons and is also evident in the hypocotyl and root (FIG. 3B). The emerging leaves of pGS3A$^{cy}$-GUS transgenic seedlings do not contain detectable levels of GUS (FIG. 3B). The absence of GUS expression in these young leaves is consistent with the apparent lack of vascularization of leaves in these young seedlings (Pato et al., 1970, Protoplasma 71:313-334). As the seedlings mature, and the leaves become vascularized, GUS activity is detected in the vasculature of pGS3A$^{cy}$-GUS transgenic seedlings. Control, F1 seedlings derived from plants transformed with a "promoter-less" GUS construct (pBI101) show no detectable GUS activity in histochemical assays. (FIG. 3C).

6.2.5. The Chloroplast GS2 Promoter Confers Light-regulated Expression on the GUS Reporter Gene Previous results have demonstrated that white light induces the accumulation of the mRNA for chloroplast GS2 in mature pea plants and in etiolated seedlings (Edwards and Coruzzi, 1989, Plant Cell 1:241-248). To determine whether the promoter for chloroplast GS2 is responsible for the light-induced accumulation of the mRNA for chloroplast GS2, the amount of GS2$^{ct}$-GUS RNA from transgenic plants grown in the light or dark was measured in a ribonuclease protection assay (FIG. 4). In two separate transgenic plants assayed, the amount of RNA corresponding to the chloroplast GS2-GUS chimeric RNA drops to undetectable levels when the mature light-grown plants are placed in the dark for 4 days (FIG. 4, lanes 1 and 3). When the dark-adapted plants are returned to white light for 24 hours, the GS2$^{ct}$-GUS mRNA accumulates approximately 8-fold (FIG. 4, lanes 2 and 4). In control plants transformed with pBI101 and grown in continuous white light, no cross-hybridization of the RNA probe with the endogenous tobacco GS mRNA is observed (FIG. 4, lane 5).

The white-light induction of the steady-state levels of GS2$^{ct}$-GUS mRNA in transgenic plants demonstrates that cis-acting elements involved in the light regulation of the pea GS2$^{ct}$ gene are contained within a 1.5 kb promoter fragment.

6.3. Discussion

Historically it has been difficult to assess the relative functions of chloroplast and cytosolic GS due to their similarities in physical properties, as well as their immunological cross reactivity. Here, the ability to localize gene expression at the single-cell level reveals that GS isoforms function in different cell types which have distinct nitrogen metabolic needs. These molecular studies have addressed previously unanswered questions concerning the cell-specific location of glutamine synthesis during plant development.

Here we have demonstrated that the promoters from the nuclear genes for chloroplast GS2 and cystolic GS3A of pea confer unique, cell-specific patterns of expression on a GUS reporter gene in transgenic tobacco plants. The promoter for chloroplast GS2 directs GUS gene expression predominantly within photosynthetically active cells, the palisade and spongy parenchymal cells of the leaf blade, in collenchymal and chlorenchymal cells of the stem, and in photosynthetic tobacco cotyledons. By contrast, the promoter for cytosolic GS3A confers vasculature-specific GUS expression in leaves, stems, and roots of the mature plant, and in the cotyledons and roots of developing seedlings. These non-overlapping patterns of GUS expression signify that the chloroplast GS2 and cytosolic GS3A isoforms perform separate functions in plant nitrogen metabolism.

The activity of the promoter for chloroplast GS2 predominantly in photosynthetic cell types is consistent with previously reported findings that chloroplast GS2 functions in the reassimilation of photorespiratory ammonia (Wallsgrove, et al., 1987, Plant Physiol. 83:155-158; Edwards et al., 1989, Plant Cell 1:241-248), and the assimilation of reduced nitrite in plasmids (Miflin, B. J., 1974, Plant Physiol. 54:550-555). Previous analysis of photorespiratory mutants revealed that plants which lacked chloroplast GS2 were inviable when grown under photorespiratory conditions even though they contained normal levels of cytosolic GS (Wallsgrove et al., 1987, Plant Physiol. 83:155-158). It has also been shown that mRNA for the chloroplast GS2 accumulates preferentially in plants grown under photorespiratory conditions whereas the levels of cytosolic GS mRNAs are unaltered (Edwards et al., 1989, Plant Cell 1:241-248). The results presented here indicate that the genes for chloroplast GS2 (GS2$^{ct}$) and cystolic GS (GS3A$^{cy}$) are expressed in distinct cell types. Therefore, in the previous analysis of photorespiratory mutants, the inability of cytosolic GS to compensate for the loss of the chloroplast GS2 activity in photosynthetic cells of mutant plants (Wallsgrove, et al., 1987, Plant Physiol. 83:155-158) may be explained by the fact that cytosolic GS and chloroplast GS2 are expressed in separate cell types, as demonstrated here. The expression of chloroplast GS2 and cytosolic GS in separate cell types may also explain why cytosolic GS gene expression is unaffected by the generation of photorespiratory ammonia (Edwards et al., 1989, Plant Cell 1:241-248). It will be interesting to determine whether expression of a GS isoform within the cytoplasm of photosynthetic cell types can functionally replace chloroplast GS2 in the reassimilation of photorespiratory ammonia.

The unforeseen finding of this transgenic analysis was the confinement of cytosolic GS3A gene expression exclusively to the vascular elements. This result has elucidated the role of this cytosolic GS isoform in plant development. While glutamine serves as a major compound for intercellular nitrogen transport in higher plants, and is found in high levels in both the xylem and phloem saps (35), its source of synthesis was heretofore unknown. From the transgenic data presented here, it is apparent that at least one cytosolic GS isoform is expressed exclusively in the phloem elements and most likely functions to generate glutamine for intercellular nitrogen transport. The high-level expression of the gene for cytosolic GS3A in the vasculature is particularly intense in the cotyledons of germinating seedlings where glutamine serves to transport nitrogen from seed storage reserves to the developing plant. These findings in transgenic tobacco correlate well with the abundant accumulation of mRNA corresponding to this gene for cytosolic GS in germinating pea cotyledons and in nitrogen-fixing nodules (Tingey et. al., 1987, EMBO J. 6:1–9), two contexts where large amounts of glutamine are synthesized for nitrogen transport (Lea et al., 1983, in Recent Advances in Phytochemistry: Mobilization of Reserves in Germination, eds. Nozzolillo, C., Lea, P. J. & Loewus, F. A. (Plenum Press, N.Y., pp. 77–109); Pate et al., 1969, Planta 85:11–34). Since expression of pea cytosolic GS3A in tobacco cotyledons is confined to the vasculature, it will be of interest to determine whether induced expression of this cytosolic GS isoform in pea nodules correlates with the vascularization of this organ. Recently, it has been shown that promoters for two cytosolic GS genes of *Phaseolus vulgaris* can direct expression in transgenic *Lotus corniculatus* nodules, and that one of these promoters is active in vascular and cortical cells of the nodule (Forde et. al., 1989, Plant Cell 1:391–401).

The quantification of GUS activity detected in whole leaf extracts of plants transformed with either pGS2$^{ct}$-GUS of pGS3A$^{cy}$-GUS revealed that plants containing the chloroplast GS2$^{ct}$-GUS transgene contained, on average, 17 times more GUS activity than plants containing the GS3A$^{cy}$-GUS construct. However, because the expression of each of the GS-GUS constructs is confined to distinct leaf cell types which comprise different fractions of the total leaf cell population, the relative amount of GUS activity in whole leaf extracts cannot be regarded as a measure of absolute promoter strength.

The light-induced accumulation of the transgenic GS2$^{ct}$-GUS mRNA reveals that the promoter for GS2$^{ct}$ contains a cis-acting DNA element involved in light regulation. Since previous experiments have demonstrated that phytochrome is partially responsible for the white-light induction of the mRNA for chloroplast GS2 (Tingey et al., 1988, J. Bio. Chem. 263:9651–9657; Edwards et al., 1989, Plant Cell 1:241–248), studies of the promoter for GS2$^{ct}$ should contribute to the understanding of phytochrome-mediated gene expression. It is noteworthy that plastid GS2 is also present in non-photosynthetic cell types such as etiolated leaves (Hirel, 1982, Planta 155:17–23) and roots (Miflin, 1974, Plant Physiol. 54:550–555). This is corroborated by the low-level of GUS expression in roots of pGS2$^{ct}$-GUS transgenic plants. Therefore, the regulation of expression of the GS2$^{ct}$ gene is likely to differ from that of other light-regulated genes which function solely in photosynthesis (e.g. ribulose 1,5 bis-phosphate carboxylase, chlorophyll a/b binding protein).

The unique expression patterns conferred upon the GUS reporter gene by the promoters for chloroplast GS2 and cytosolic GS3A and the light-regulated induction of pGS2$^{ct}$-GUS RNA levels are most likely due to the transcriptional regulation of these transgenes. However, because the GS-GUS fusions contain the 5' non-coding leader of the GS mRNAs and a small portion of the GS coding regions, it is possible that post-transcriptional events (e.g. RNA stability, translational regulation, and subcellular compartmenalization) also contribute to the observed differences in transgene expression. Future experiments directed at characterizing the specific cis-acting regulatory regions of the GS genes will distinguish between these possibilities.

In addition to elucidating the individual roles of the GS isoforms in plant nitrogen metabolism, the transgenic studies presented here describe plant promoters which may be used to direct cell-specific expression of foreign genes in plants. In particular, a promoter which confers specific expression of foreign genes in phloem cells has potential application in generating resistance to viral pathogens transmitted within the phloem (Schneider, 1965, 11:163–221). Finally, since glutamine synthetase is the target of several herbicides (Kishore, et al., 1988, 57:627–663), the expression studies presented here indicate that it may be necessary to express herbicide resistant forms of GS in both photosynthetic and vascular cell types in order to confer resistance to GS inhibitors.

Nucleotide analysis of the GS genes in *P. sativum* has shown that chloroplast and cytosolic GS are derived from duplications of a single ancestral gene followed by specialization of each locus for distinct expression (Tingey et al., 1988, J. Bio. Chem. 263:9651–9657; Coruzzi et al., 1989, in The Molecular Basis of Plant Development, Alan R. Liss, Inc., pp. 223–232). Future studies directed at the identification of the necessary cis-acting promoter regions of the nuclear genes for chloroplast and cytosolic GS should uncover DNA elements which have evolved to confer distinct spacial and temporal patterns of expression to these genes.

7. EXAMPLE: IDENTIFICATION OF A REGION OF THE GS3A PROMOTER REQUIRED FOR EXPRESSION IN TRANSGENIC PLANTS AND A DNA-BINDING PROTEIN WHICH BINDS TO THIS GS3A ELEMENT

In the examples detailed below, the DNA sequence of the pea cytosolic glutamine synthetase GS3A gene promoter was determined and the start of transcription mapped using S1 nuclease. The full-length promoter and a series of 5' deletions were ligated to $\beta$-glucuronidase (GUS) and introduced into transgenic tobacco and alfalfa. In transgenic tobacco, the GS3A promoter directed GUS expression in the phloem cells of the vasculature in leaves, stems, and roots. GUS expression was also detected in the vasculature of cotyledons, and the root tips of germinating T1 seedlings. The promoter conferred a similar expression pattern in transgenic alfalfa, and expression was also observed in root nodules. Nodule expression was located in nodule primordia, and the meristem, the symbiotic zone, and vasculature of mature nodules. The promoter was found to be active even when deleted to $-132$ relative to the start of transcription (FIG. 5B, nucleotide number $-132$;

SEQ. ID. NO. 2, nucleotide number 1701). DNA mobility-shift analysis identified a protein present in nuclear and whole cell plant extracts which bound to a 17 bp DNA element contained within the minimal −132 promoter required for expression (FIG. 5B, nucleotide number −122 to −106; SEQ. ID. NO. 2, nucleotide number 1711 to 1727).

The DNA sequence of the promoter of the GS3A gene, the expression patterns the full-length promoter, and a series of 5' deletions in both transgenic tobacco and transgenic alfalfa were analyzed. We identified a region of the promoter which is required for expression in both tobacco and alfalfa and which directs GUS expression at high levels in cotyledons and nodules. This promoter fragment was subsequently used to identify a novel DNA-binding protein present in nuclear and whole-cell plant extracts.

7.1. Materials and Methods

7.1.1. DNA Cloning and Sequencing

A clone carrying a 5.76 kb insert was isolated from a genomic library of Pisum sativum cv. 'Sparkle' constructed in 'lambda dash' (Stratagene) using the GS3A (a.k.a. GS341) cDNA as a hybridization probe (Tingey et al., 1987, EMBO J. 6: 1-9). Standard procedures were used for library screening and plaque purification. The 5.76 kb insert was transferred to pEMBL18 for sequencing using the dideoxy chain-termination (Biggin et al., 1983, Proc. Natl. Acad. Sci. USA 80: 3963-3965; Murphy and Kavanagh, 1988, Nuc. Acids. Res. 16: 5198).

7.1.2. S1 Nuclease Mapping

The transcriptional start site of the GS3A promoter was mapped by 5' S1 analysis. A uniformly labelled DNA probe was prepared using the oligonucleotide EW1 (extending from +85 to +104) as a primer on a GS3A genomic clone template corresponding to the deletion A16 cloned in M13mp18. Restriction digestion of the labelled product within the M13mp18 polylinker yielded a probe of 332 bp. This DNA probe was hybridized to total RNA from leaves, roots, 21 day old nodules and cotyledons of 5 day old seedlings, all from pea. Following incubation with S1 nuclease, the products were separated on a 5% denaturing polyacrylamide sequencing gel. Dideoxy sequencing reactions of the DNA probe also primed by EW1 were run alongside the S1 nuclease digestion products.

7.1.3. Construction of Promoter-GUS Fusions

A GS3A promoter-containing fragment extending from the BamHI site at −1832 (SEQ. ID. NO. 2, nucleotide number 1) to the BglII site at +103 (SEQ. ID. NO. 2, nucleotide number 1935) was transferred to 'pTZGUS', that is pTZ18U into which the β-glucuronidase coding sequence and nopaline synthase terminator from pBI101 had been transferred as a HindIII-EcoRI fragment. This created a promoter-GUS translational fusion incorporating six amino acids from the amino terminus of GS3A and nine amino acids derived from polylinker sequence and the GUS leader (see FIG. 8). This construction retained the HindIII, SphI, PstI and SalI restriction sites of the polylinker upstream of the promoter fragment and was therefore suitable to generate 5' deletions in translational fusion. Digestion with PstI and SalI was followed by incubation for various periods of time with exonuclease III, and subsequently exonuclease VII and T4 polymerase (Murphy and Kavanagh, 1988, Nuc. Acids Res. 16: 5198). Deleted plasmids were recircularized using T4 DNA ligase and transformed into E. coli DH5α. DNA was prepared from 10 ml cultures (Murphy and Kavanagh, 1988, Nuc. Acids Res. 16: 5198), and the extent of deletions determined by dideoxy sequencing. Suitable deletions were excised from pTZ by SphI-EcoRI digestion and transferred to pBin19 (Bevan, 1984, Nuc. Acids Res. 12: 8711-8721) between the HindIII and EcoRI sites using a HindIII-SphI adaptor-linker.

7.1.4. Plant Transformations

Binary vector constructions were transferred into the disarmed Agrobacterium strain LBA4404 by triparental mating using the procedure described by Bevan (1984, Nuc. Acids Res. 12: 8711-8721). The same mated Agrobacterium were used for both tobacco and alfalfa transformation. Nicotiana tabacum genotype SR1 was transformed by a leaf inoculation procedure (Horsch et al., 1985, Science 227: 1229-1231), and regenerated shoots were selected on medium containing 200 µg/ml kanamycin. Primary transformants were maintained in sterile culture and subsequently grown to maturity in soil. T1 seeds were sterilized in 10% sodium hypochlorite and germinated in medium containing 100 µg/ml kanamycin and 500 µg/ml carbenicillin. Medicago varia genotype A2 was transformed using a co-cultivation procedure previously described by Deak et al. (1986, Plant Cell Reports 5: 97-100). Stem internodes were co-cultivated with Agrobacterium in liquid culture containing 1 mg/l 2,4-D and 0.2 mg/l BAP. Subsequently transformed callus was selected on plates containing the same hormones and also 50 µg/ml kanamycin. Selected callus was recultured in liquid medium without kanamycin and redifferentiated somatic embryos were grown up on plates without hormones and transferred to soil as soon as substantial root growth was observed. Nodulation was induced on primary transformants by treating roots with 'N' medics VN-1 Rhizobium inoculant supplied by Liphatech (Milwaukee, Wis., USA).

7.1.5. Analysis of GUS Expression

Histochemical staining of tissues was done as previously described (Jefferson, 1987, Plant Mol. Biol. Rep. 5: 387-405; Jefferson et al., 1987, EMBO J. 6: 3901-3907). After incubation with the GUS substrate, 5-bromo-4-chloro-3-indolyl-β-D-glucuronic acid (Clontech), cross-sections of organs and seedlings were cleared of chlorophyll by incubation with a solution of 5% formaldehyde, 5% acetic acid, and 20% ethanol for 10 minutes followed by 2 minute incubations with 50% and 100% ethanol. For thin sections material was embedded in 'Paraplast Embedding Medium' (Oxford Labware, St. Louis, Mo., USA), and 8 µm sections cut and stained briefly with erythrosin (Berlyn and Miksche, 1974, Botanical Microtechnique and Cytochemistry, Ames, Iowa; Iowa State Univ. Press). Photomicrographs were taken with a Nikon Optiphot microscope using phase-contrast optics.

Fluorometric GUS enzyme assays were done as previously described (Jefferson et al., 1987, Plant Mol. Biol. Rep. 5: 387-405). Five µg of protein were incubated with 4-methylumbelliferyl glucuronide (MUG) solution for 15 minutes after which 2.5 ml of 0.2M sodium carbonate were added. Fluorescence was measured with a Perkin Elmer LS5 fluorimeter. Fluorescence of a solution of 0.1 mM 4-methylumbelliferone (MU) in 0.2M sodium carbonate was used for calibration.

7.1.6. DNA Mobility Shift Analysis

Fragments for DNA mobility-shift analysis were synthesized as oligonucleotides, and complementary oligonucleotides annealed and cloned into pTZ19U derived vectors. Fragments were excised from the vector, purified by polyacrylamide gel electrophoresis, and then end-labelled with $^{32}$P-dATP, $^{32}$P-dCTP, $^{32}$P-dGTP, $^{32}$P-TTP using the Klenow enzyme. DNA-protein binding was done for 30 minutes at room temperature in 20 mM Hepes-KOH pH 7.5, 40 mM KCl, 1 mM EDTA, 10% glycerol (Katagiri et al., 1989 Nature 340: 727-730). Five μg sonicated polydIdC (Pharmacia) was used as nonspecific competitor DNA. Whole-cell and nuclear extracts were prepared as previously described (Green et al., 1987, EMBO J. 6: 2543-2549; Green et al., 1989, Plant Molecular Biology Manual B11, pp. 1-22.

7.2. Results

7.2.1. GS3A Promoter Sequence and Determination of the Transcriptional Start Site A genomic clone was isolated using the GS341 cDNA (Tingey et al., 1987, EMBO J. 6: 1-9) as a hybridization probe; based upon sequence analysis, was subsequently shown to encode the GS3A gene. FIG. 5B shows the sequence of the GS3A promoter extending from −1832 relative to the start of transcription to +107 (SEQ. ID. NO. 2, numbers 1 to 1939). S1 analysis located the start of transcription to both of two adenosines underlined in FIG. 5B. For the purposes of consistency we notate the second A as +1 (SEQ. ID. NO. 2, nucleotide number 1833). The transcriptional start site was mapped using RNA from several organs to determine if transcription initiation was identical in organs as diverse as cotyledons and root nodules. The results of this analysis indicate that identical transcription start sites are utilized in leaves, roots, nodules, and cotyledons (FIG. 7).

7.2.2. Deletion Analysis of the GS3A Promoter in Transgenic Alfalfa and Tobacco A series of 5' promoter deletions of GS3A were ligated to GUS and introduced into tobacco and alfalfa by Ti-mediated DNA transfer. Deletions were made in translational fusion at +107 (SEQ. ID. NO. 2 at 1939) using the BglII site, and therefore include 19 bp of the GS coding sequence (FIG. 8). As described in Section 6, supra, a translational fusion of −903 bp (SEQ. ID. NO. 2 at 929) assayed in transgenic tobacco was found to confer phloem-specific expression. Our aim was to assess the expression pattern of GS3A promoter fragments up to approximately 2000 bp driving β-glucuronidase expression, to identify which promoter elements were responsible for the phloem-specific expression pattern, and to compare this activity to the expression pattern found in the legume alfalfa, in particular in alfalfa nodules.

All six promoter deletion constructions of GS3A assayed in transgenic plants conferred the identical pattern of GUS expression. In tobacco the full-length GS3A promoter construction (FIG. 8, A28), as well as five deletions (FIG. 8, A45, A22, A16, A13, A10), were found to confer GUS expression in phloem cells in leaves, stem, and roots of primary transformants. These same constructs also conferred vasculature-specific expression in cotyledons and in root tips of T1 seedlings (FIG. 9). Transgenic alfalfa plants were produced using four of these constructions (A28, A22, A13, and A10). All four constructs expressed GUS, and expression was again localized to the phloem cells of the leaf (FIG. 10, panel F), stem (FIG. 10, panel G), and root (FIG. 10, panel C) vasculature, and additionally to root tips. Following nodulation, expression was observed in developing nodules. The GS3A promoter directed GUS expression at early stages of nodule formation in the nodule primordia (FIGS. 10A and 10B), and as nodule development proceeded, GUS expression was highest in the meristem and early symbiotic zones and undetectable in the senescent zone (FIG. 10, panels C, D, J, K and L). GUS expression was also visible in the vascular elements around the central infection zone (FIG. 10E). Control nodules formed on plants transformed with pBI101 showed no GUS expression (FIG. 10, panel I).

The comparative analysis of GS3A deletion constructions in transgenic tobacco and alfalfa revealed that the cis-elements responsible for the expression patterns observed are conserved between legumes and non-legumes, and are contained in the smallest deletion extending to −132 relative to the start of transcription (SEQ. ID. NO. 2, number 1701). Furthermore, the −132 GS3A promoter deletion confers expression in phloem cells of leaves, stems, roots, cotyledons, and nodules, in root tips and also in the meristem and symbiotic zone of nodules. This 132 bp promoter fragment may therefore contain a single cis-element which activates transcription in phloem, meristem, and the infected cells of nodules, or alternatively it may contain multiple elements.

Quantification of GUS expression in leaf, stem, root, cotyledon, and nodule tissue using the GUS fluorometric assay demonstrated that expression was always strongest in nodules, and on average approximately ten times higher than that observed in leaves. Stems and roots showed intermediate expression (see Table II).

TABLE II
FLUORIMETRIC QUANTIFICATION OF GUS ACTIVITY

| Organ | GUS ACTIVITY* | | | | | | |
|---|---|---|---|---|---|---|---|
| | 1 | 2 | 3 | 4 | 5 | 6 | 7 |
| leaf | 1800 | 414 | 26 | 238 | 101 | 150 | 455 |
| stem | 7480 | 97 | 9 | mv | 26 | 730 | 1668 |
| root | 9372 | 339 | 84 | 207 | 268 | mv | 2054 |
| nodule | 13275 | 708 | 937 | 4088 | 2077 | mv | 4217 |

*Values of GUS activity for leaf, stem, root, and nodules from 6 alfalfa transformants are expressed in pmol of MU per mg protein per minute. Transformants 1 and 2 are A28 constructions, and 3, 4, 5, and 6 are A13 constructions. Column 7 expresses tissue means; mv-missing value.

7.2.3. A DNA Element Within the GS3A −132 Promoter Binds to a Factor Present in Plant Extracts DNA elements contained within the −132 GS3A promoter were used in DNA mobility-shift assay to identify DNA binding proteins in plants extracts which may play a role in the transcriptional activation of the gene. Mobility-shift assays were undertaken with radiolabelled DNA fragments spanning the −132 GS3A promoter; these fragments are shown FIGS. 11A, 11B and 11C. Fragment a201, which extends from −129 to −97 relative to the start of transcription (SEQ. ID. NO. 2, from nucleotide number 1704 to 1736), was found to bind a factor which was designated GS3A-F1. GS3A-F1 was present in whole-cell extracts of pea, and nuclear extracts of pea and tobacco; it was sensitive to boiling and treatment with proteinase K, indicating the proteinaceous nature of GS3A-F1. Fragments a202

(−129 to −106; SEQ. ID. NO. 2, 1704–1736) and a206 (−122 to −106; SEQ. ID. NO. 2, 1711 to 1727) also bound GS3A-F1, although a206 exhibited lower affinity (FIG. 11B). In all cases, self-competition with unlabelled fragment was effective at relative molarities of between 10 and 50-fold excess. In cross-competition experiments, unlabelled fragment a202 was able to compete for factor binding to radio-labelled a206 (FIG. 11B). The binding of GS3A-F1 was shown to be specific for its target sequence within a201, in that unlabelled DNA competitor corresponding to the DNA binding sites of cloned transcription factors were unable to compete with a201 for GS3A-F1 binding. Data for competitions with the rbcS-3A GT1 binding site and corresponding mutant are shown in FIG. 11C (Green et al., 1988 EMBO J. 7: 4035–4044). Additionally, binding to GS3A-F1 was not competed by the DNA binding sites of 3AF1 or ASF1 (Lam et al., 1990, Plant Cell 2: 857–866; Katagiri et al., 1989, Nature 340: 727–730).

The overlapping region of a202 and a206 is a core of 17 nucleotides which contains an imperfect inverted repeat. Fragment a206 contains an imperfect palindrome, and this was bisected by fragments a230 (−173 to −114; SEQ. ID. NO. 2, 1660 to 1719) and a239 (−113 to −54; SEQ. ID. NO. 2, 1720 to 1779), neither of which were able to bind GS3A-F1. However, when used as unlabelled competitors, both a230 and a239 were able to decrease the binding of GS3A-F1 to a201 and a202 (FIG. 11). This analysis shows that a minimum of 17 bp of the GS3A promoter from −122 to −106 (SEQ. ID. NO. 2, 1711 to 1727) relative to the start of transcription are required for GS3A-F1 binding. This result may provide an insight into the mode of binding of GS3A-F1. It is possible, for example, that a stable DNA-protein complex forms only when GS3A-F1 binds as a dimer to the target DNA and that the 17 bp imperfect palindrome provides a secondary structure to enable such binding. Unlabeled a230 and a239 may compete for monomeric GS3A-F1 and disrupt complex formation without themselves forming a stable interaction with GS3A-F1 detectable by DNA mobility shift assay.

7.3. Discussion

Using the GUS reporter gene, the experiments described in the examples herein demonstrate that the pea GS3A promoter is expressed in a phloem-specific fashion in both transgenic tobacco and in transgenic alfalfa. The pattern and degree of promoter activity is reflective of glutamine synthesis in phloem cells and the significance of glutamine as a long-distance nitrogen transport compound; i.e., the GS3A gene is expressed at highest levels in pea organs where large amounts of nitrogen are mobilized. Quantification of GUS expression demonstrated that GS3A activity was indeed highest in root nodules of transgenic alfalfa. Expression in nodules was found not only in the vasculature but also in the meristem and the symbiotic zone, where Rhizobia actively fix atmospheric nitrogen; expression was substantially lower in the senescent zone of the nodule in which fixation no longer occurs. Apart from expression in root tips, the activity of the promoter was localized to the phloem cells of the vasculature in all organs examined.

The pattern of GUS expression conferred by the GS3A promoter in transgenic alfalfa differs from that described for GS promoters from *Phaseolus Vulgaris* and soybean GS when introduced into transgenic *Lotus corniculatus*. Expression of the *Phaseolus vulgaris* gln-γ gene in Lotus corniculatus was restricted to infected cells of the nodule. The gln-β gene promoter of Phaseolus directed GUS expression in cortical and infected cells of young nodules, and became restricted to nodule vasculature in older nodules of transgenic *L. corniculatus* (Forde et al., 1989, Plant Cell 1: 391–401). A soybean GS promoter induced GUS gene expression in the central infected zone (including the uninfected cells) of transgenic *L. corniculatus* (Miao et al., 1991, Plant Cell 3: 11–22). Since glutamine synthesis and transport may vary in amide (pea, alfalfa, Lotus) and ureide transporting plants (soybean, Phaseolus), the selection of a specific host plant may influence the regulation of a heterologous GS promoter. Alfalfa was selected as the host legume for the transgenic studies described infra as it possesses determinate nodules similar to those of pea, and both pea and alfalfa are physiologically similar in transporting nitrogen primarily as the amides glutamine and asparagine (Pate et al., 1969, Planta 85: 11–34; Newcomb, 1976, Can. J. Bot. 54: 2163–2186; Newcomb, 1981, Int. Rev. Cyt. Suppl. 13: 247–297). The striking feature of GS3A promoter-GUS expression in our experiments is the high level expression in the nodule meristem of transgenic alfalfa. In this context it is interesting that a persistent meristem is one of the morphological features conserved amongst plants with indeterminate nodules (e.g. pea and alfalfa).

By promoter deletion analysis we were able to define the region of the GS3A promoter involved in its phloem-specific, cell-specific and developmentally-regulated expression. A short DNA element of GS3A (position −132 to +107 indicated in FIG. 5B; SEQ. ID. NO. 2 nucleotide numbers 1701 to 1939) was functional in both tobacco and alfalfa and was qualitatively equivalent to the full-length promoter in its expression. DNA fragments a201, a202 and a206 contained within the −132 GS3A promoter element (shown in FIG. 11A) were found to bind a proteinaceous factor, GS3A-F1, found in whole-cell extracts of pea, and nuclear extracts of pea and tobacco.

The results described above indicate that the cis-regulatory sequences of the GS3A gene, which function to promote expression in nodules, are also able to promote high level expression in cotyledons, suggesting that the transcription factors involved in promoting gene expression are not confined to nodules. This is consistent with our observation that the same transcription initiation site is utilized in cotyledons and nodules. Furthermore, it is compatible with the finding that at least one nuclear protein factor which interacts with the GS3A promoter (GS3A-F1) is present in both pea and tobacco extracts.

The high level of expression of GS3A in cotyledons and nodules suggests that a common signal induces GS expression in these organs. The generation of catabolic ammonia has previously been suggested as a metabolic inducer of GS gene expression (Miao et al., 1991, Plant Cell 3: 11–22; Hirel et al., 1987, EMBO J. 6: 1167–1171). It has been reported that ammonia regulates the expression of GS in soybean (Hirel et al., 1987, EMBO J. 6: 1167–1171), and more recently Miao et al. (1991, Plant Cell 3: 11–22) have demonstrated that the promoter of a soybean GS gene was able to confer ammonia inducible expression in transgenic plants. By contrast, analysis of GS expression in fix-nodules demonstrates that ammonia is not required for induced expression of GS in nodules of pea, Phaseolus, and alfalfa (Walker and Coruzzi, 1989, Plant Physiol. 91: 702–708; Cock et al., 1990, Plant Mol. Biol. 14: 549–560; Dunn et al., 1988, Mol. Plant-Microb. Interact. 1: 66–74). Furthermore, our finding that the GS3A-GUS transgene is expressed in nodule primordia formed long before the onset of nitrogen-fixation corroborates the conclusion that newly fixed ammonia is not required for activation of GS3A transcription in nodules.

A further possibility is that GS gene expression is mediated by plant hormones in both nodules and cotyledons. It is curious that the 17 bp element of the GS3A promoter contained within a206 (indicated in FIG. 5B; SEQ. ID. NO. 2 from 1711 to 1727) which binds the protein factor GS3A-F1 is itself palindromic and similar to the palindromic mammalian steroid response element (Evans, 1988, Science 240: 889–895). This homology is intriguing because GS expression in animals has been shown to be steroid-induced in at least one mammalian cell line (Miller et al., 1978, Proc. Natl. Acad. Sci. USA 75: 1418–1422). The factor GS3A-F1 is present in both pea and tobacco extracts and this is consistent with the activity of the GS3A promoter in both these species. We also note the existence of a sequence with homology to the previously described nodulin consensus (Forde et al., 1990, Plant Cell 2: 925–939) at nucleotides −106 to −101; this sequence was not, however, involved in the binding of GS3A-F1 or any other factor that we were able to detect in plant extracts.

8. DEPOSIT OF MICROORGANISMS

The following microorganisms have been deposited with the Agricultural Research Culture Collection, Northern Regional Research Center (NRRL) and have been assigned the following accessin numbers:

| Microorganism | Plasmid | Accession No. |
| --- | --- | --- |
| Escherichia coli XL1 | pGS2ct-1/1583 | B-18575 |
| Escherichia coli XL1 | pGS3Acy-1/1941 | B-18576 |
| Escherichia coli XL1 | pGS3Acy-931/1941 | B-18577 |
| Escherichia coli XL1 | pGS3Bcy-1/1248 | B-18578 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 1601 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
CTATACTACG TGGAATTCAG AAAGGAAAGG GAAAGACTCT TCAGATGTTG GAAGCAAGGA      60
AGAGGCCTAT ATAAAGGACA TGAAGAAATG AGGAATATGT GGGCGCAGAA TCACATGAGA     120
AAATACTTGA ATACACTTAA ATCAATTATT TTTATACTCT CCTTGACGAA TAACGGGGAA     180
GTCAACCTTT TAGTATTTTT ACCAAGAATA CACAAATAAA TAGAATCTAA TTCTTTTAAT     240
AGAAATCAAT TATCCGAGTC ACACAATTGC TGCGATTAAT TTCTCGAGTA GAATTTGATT     300
AAAACTAAAT ATACATAAAT GAGTGAGAAC ACCAAATAAA TAAAATTATA AAAAATAATA     360
TTATAATGTA TTAAGATGAT AAAGTATAAT TAACTTTAGA CTTAAATGAG TTTTTTTTTT     420
ACTCTTCCAT TATTTTATTT GGAGTTTCCC CCCATTTTTT AAATCCCAAA ATAATGTTAC     480
TTATGTGCTA ATTTGTCAAA TCATAGTTTT GATATTAAAA TTTTCAAATA TATTGTAATG     540
CTACATAAGT TTCACGTGCA TTATTTCTCA ATCATCATAT TTACTACTAA ATGTTAAAAT     600
TTGACATAGA AATCAAAATT GTATAAATTC AAAAACTATA TAATCATAAT TGCAAATTAA     660
TGTTTCTAAG CAAAGCAACT TAAGTTAAGA AGATCTAAGC AAAGATACAA AGATATTGTC     720
AACATAGAAT TTAGTAATCA TTATTCATTG TAGTTATAGA ATCTAAACAT GAAAATTAAT     780
TGGATAAAAA AAGAAAGAGA AATCCTTATC TAAATATTGA AAGTCCAAGC TTCTCTTGGT     840
GCTCTTTAAG GGACCAAAAA CAAACTTCAT CCACTCAAAA ACTCACCCCT ATCGTTATTG     900
CAATAGCCAA CAAACTTGTT TTCTTGCCCA CCACCAACCC TTATTTACA CAACTCTCTC      960
```

| | | | | | |
|---|---|---|---|---|---|
|TCACTCTCTA|TTGCTCCATT|GACACAAGGC|TCATTCTCAC|TTGAACCCAT|TTTCAACCTT|1020|
|TGCTGTTTTT|GCCATTTTTC|AACTCTGTAT|TGGTGAGTTT|CTTTCTACCT|TCAATACCAT|1080|
|TTTCGTCCTT|TTTCTTAAAC|GTTTATTTAT|GACATTCAAA|ATTCAATCTT|TGTAGTTTCT|1140|
|TGCTAGTGAA|AATTTATGAT|GGTTCTTTGA|ATATACTTTA|GCTTCATGCA|AAACTAACTT|1200|
|CTTTATCATT|TTGAGCAAAT|TGATGTTTAG|TAGCTATGAA|AGAATTTGGA|TCTGATTAAT|1260|
|CACTTTGTTT|TATTGTGTTA|TATCTAAATA|TGATTCCAAA|AAGCAATGCT|CTTGGTAAAC|1320|
|TTTACTCTCT|TTTATGTTAG|TTAGATATTT|TCTTGAATGA|TTATTTACTT|CTTGGTTGGT|1380|
|TTTTTGCAAT|GTGCATCTTA|ATAGAATGCT|GTTTGATTCT|TTTTTTTTTT|GTTGAGTAGA|1440|
|AAATGGCGCA|GATTTTGGCA|CCTTCGACGC|AATGGCAGAT|GAGAATCACA|AAAACCTCTC|1500|
|CTTGTGCAAC|TCCAATCACA|TCAAAGATGT|GGAGTTCTTT|GGTTATGAAA|CAAACTAAGA|1560|
|AAGTTGCGCA|TTCTGCTAAA|TTTAGAGTTA|TGGCAGTCAA|C| |1601|

(2) INFORMATION FOR SEQ ID NO:2:

(i) SEQUENCE CHARACTERISTICS:
        (A) LENGTH: 1939 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

| | | | | | |
|---|---|---|---|---|---|
|GATCCTCTAG|CCTATCAAGG|AGTAATATCT|ATCATATCTA|ACTCTGGACC|CATTTACTTG|60|
|GATCTAGTTA|GAGAATTTTA|TGTAAATTTA|TCAATTGGTA|CTGGGTGCAT|TTTGTAATCA|120|
|AAAGTGAAGG|ACAAAAATAC|TGTAAATTTA|TCAATTGGTA|ATGGACATGA|CAAAGTACCT|180|
|AATTCACCCC|TCCCTCCTCT|TAGGTGCATT|CCATACTTAC|AATAGTTTAT|ATAATTGGAT|240|
|TGGACATAAC|ATCGATGGTG|GCTCTACCTT|TTTGGTTGCT|TGCTGATAGT|TGCGTTGCGC|300|
|TAGGAACAAA|TTGTGTCTTG|CTAATGAAAT|TGTATCTTCA|TATACTTTGA|AACTCATAAC|360|
|AATGAATTGT|GCTAATCTGT|TAGCTAAATG|TTTTCTCAAG|CAGTGTCTTA|TCTAATTAGA|420|
|ACGATCACGT|GGAATGCACA|CAAAGGTAGT|AATATAATTT|TGAATGTTAA|TGACAGTAGC|480|
|CTCAGTAATC|CCGACGTCTC|AAGTTTGGT|GGGTTGATTT|GAAGTGTTGA|TGGTGTTTGG|540|
|GTTCACGATT|TTGTGGGTAA|TATTGGTTAT|TCCAATATCC|TTCATGTTGA|GTGATTGCAT|600|
|TATATCATGC|TTTGTGTATG|ACCTAAAAAC|TTGGCCAGTG|AAGACTTGAG|GTGTTATTCT|660|
|AACTCCAACT|CTATTATCAA|GCTTATCACA|TAGTCGGTTA|ATGTTTAACA|TCACTGTGCT|720|
|GCTAATCTTC|ACAATATTAA|AAAACTGGTC|TCTTAGGAAT|GCCGGGTTCA|AATATTTCTA|780|
|CTCTTAGGAA|GAAGAATGTT|TGTGTTGACT|ATCTAGCAAA|ACATGGAACT|GACAATGATG|840|
|CGGCGTACCA|GTCTTTTGCA|GAGCCTACTA|TAGGAATCAT|CACTCACTTA|CTAGTTGGCG|900|
|CTAGTGAGAT|TTATTTTTT|AAATAATTTT|TTTTCTTTTC|CTTTTTTACT|TGTACAAAAA|960|
|AAATATTCAA|GTTCAAAAAA|AAGAAAAAA|AATTATTTGA|ATTTAAAATA|AAAATCAAAA|1020|
|ATGAAAAATC|AAATAAAATA|GAGAACACTA|TTTTCAATTA|AATTCTTTTA|TTAAATACAT|1080|
|GAATAAAAAC|TAAATAATAT|AATAATGATC|TTTAACTTTA|AATACTAATT|CATATAATAA|1140|
|TAAAAACTAA|CTATAAGAAT|ACTAACAATA|AACTTTAATT|GCTTTATTAA|GTCATCTATA|1200|
|ATAGAGAAAT|TCAATAATAA|CAAGTTGAA|TTGTGAAATT|TTGATTATTA|GATACTAAAG|1260|
|AGTGAAATTT|TAATTATTAG|ATATTTAATA|AAAATATTAT|TTTAAAATAG|TATACTTTAA|1320|
|TTTGAATTAA|TATTTAAAGT|TGTATTACAT|AGAACTTTAC|AAATGCTAAA|TAAAATTATT|1380|

| | | | | | | |
|---|---|---|---|---|---|---|
| TTGAATCAAA | ATATAAAATA | AATATAATAT | AGTTTTACCA | AAAAAAAAAT | ATTAATTAAG | 1440 |
| TGAAGTATCC | TACCAACCAC | ATATTAATTA | GATAATTATA | TTAAAAAACA | TACTTTTCCG | 1500 |
| TACATTGCTT | CTCATAAAAA | TATCATTTAT | CTATAAGACA | GAATCATATC | TACACCGCAA | 1560 |
| ATTATTCTCA | TTAGATTCGT | AAAAGAATT | CAAGTTATC | ATATCCTTTC | CTTTCTTTT | 1620 |
| AGAAAAAAT | TAAGTGATAA | TCTATTTTAT | TTCATTTCTA | TCTTTAAGAA | ATTAAAAAAT | 1680 |
| AACCATTTTA | TTCCAATTTT | CAAAATTCAA | TTGATCTAGT | AGATAAAAAG | ATTCTCCGAA | 1740 |
| GACAACCACT | AAAAGTTAA | TAACAATTTA | ATAGTAATTT | TTTCTACATA | TCATTCTATT | 1800 |
| ATAAATAGGT | TCATATCTCA | CACTTTCTTT | TAACCCTTAC | AAAAAGCCAG | AGATTCCTCT | 1860 |
| GTAGCTATCT | TTCAACAAAA | CCGCGTTCTT | CTTTTCCTT | CAAAGCTTTT | CATTATCATT | 1920 |
| ATGTCTTCAC | TTTCAGATC | | | | | 1939 |

(2) INFORMATION FOR SEQ ID NO:3:

(i) SEQUENCE CHARACTERISTICS:
        (A) LENGTH: 1262 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

| | | | | | | |
|---|---|---|---|---|---|---|
| GTTAAACACT | GCTGCAGAAT | ATGACTATGG | GCTCTAAAGA | AAGCTTCAAA | GAATATGCTC | 60 |
| AAAAATGGAG | AGACTTGGCT | GACAGAGTCA | AACCCCTAT | GACTGATCGA | GAATTAGTGG | 120 |
| ACATGTTCAT | GGGTACACTG | ACTGGCCCAT | TCTACAGCCA | TATATTGGGA | AGTTCCTCAT | 180 |
| CGGGTTTCAC | TGAACTTATA | TTTACGGGTG | AACGTGTTGA | ACGCGGCATT | CGAAGTGGAA | 240 |
| AGATACATGC | GGCTACCTCT | GCAAGCACAA | AAAGTCCTA | TCAAGGGAAG | AATGAATCAA | 300 |
| ATGCTGTGTA | CGGTCAAAGG | GGTCATAACA | AGAAAAATCG | TGACCATACT | GTTGGAGCAG | 360 |
| TTACGATTGC | AGCACCGCCA | TCTCAAAACT | TCCAACACAG | ACAAGACAGG | CCAAGAAGGC | 420 |
| AGTTTACCAA | GATCAATATG | ACTTTAGCAC | AAGCACTGTA | GGGTATGCTA | AAAGCAAATT | 480 |
| TAATTACCCT | CAGAGATCCT | CCTGCAAATC | CCAACACTAC | TTCTCCTCGT | TATAATCCCA | 540 |
| ATGCCAGGTG | TGCATATCAC | TCCGATAGCC | CCGGGCATGA | TACAAACGAT | TGTTGGTTGT | 600 |
| TGAAGAATAA | GATTCAGGAT | ATGATCGACG | CTGGAGAAAT | TGAATTTGAT | CCTTCGGAGA | 660 |
| CTCCTAATGT | CATCACTGCT | CCAATGCCTA | ATCATAACAA | GACTATTAAT | GTTGTGGATG | 720 |
| ACATACTTAA | AAAATATTCT | TTTTCATACA | TATTAATTAA | ATGAAGTATC | CTACCAACCA | 780 |
| CATATTAATT | AAATAATTAT | ATTAAAAAAC | ATACTTTTTC | ATACATTGCT | TCTCATAAAA | 840 |
| ATATCATTTA | TCTATAAGAC | AGAATCATAT | CTACACCGCA | AATTATTCTC | ATTAGATTCA | 900 |
| TAAAAGAAAT | TCAAGTTAT | CATATCCTTT | CCTTTCTTT | TAGAAAAAAA | TTAAGTGATA | 960 |
| ATCTATTTTA | TTTCATTTCA | ATCTTTAAGA | AATTAAAAAA | TAACCATTTT | ATTCAATTTT | 1020 |
| CAGAATTCAA | TTCATCTAGT | AGATAAAAAG | ATTCTCCTAA | CACAACCACT | AAAAAGTTAA | 1080 |
| TATCAATTTA | GTAGTAATTT | TTTCTACATA | TCATTCTATT | ATAAATAGGT | TCATATCTCA | 1140 |
| CACTTTCTTT | TAACCCTTAC | AAAAAGCCAG | AGATTCCTCT | GTAGCTATCT | TTCAACAAAA | 1200 |
| CGCGTTCTTC | TTTTTCTTC | AAAGCTTTTC | ATTATCATTA | TGTCTTCACT | TTCAGAAGAT | 1260 |
| CT | | | | | | 1262 |

What is claimed is:

1. A substantially pure GS3A glutamine synthetase promoter element which is a pea GS3A promoter element or a portion of the pea GS3A promoter element, that confers vasculature-specific expression in the leaf, stem and root of a mature plant to an operably associated coding sequence.

2. A substantially pure GS3A glutamine synthetase promoter element of claim 1 having a nucleotide sequence as depicted in SEQ ID NO:2 from nucleotide residue number 1701 to 1832 or a portion of said depicted sequence.

3. A substantially pure GS3A glutamine synthetase promoter element of claim 1 having a nucleotide sequence as depicted in SEQ ID NO:2 from nucleotide residue number 1704 to 1736 or a portion of said depicted sequence, wherein said depicted sequence is:
AATTCAATTGATCTAG-
TAGATAAAAAGATTCTC.

4. A substantially pure GS3A glutamine synthetase promoter element of claim 1 having a nucleotide sequence as depicted in SEQ ID NO:2 from nucleotide residue number 1704 to 1727 or a portion of said depicted sequence, wherein said depicted sequence is:
AATTCAATTGATCTAGTAGATAAA.

5. A substantially pure GS3A glutamine synthetase promoter element of claim 1 having a nucleotide sequence as depicted in SEQ ID NO:2 from nucleotide residue number 1711 to 1727 or a portion of said depicted sequence, wherein said depicted sequence is:
TTGATCTAGTAGATAAA.

6. A recombinant DNA molecule containing a GS3A glutamine synthetase promoter element which is a pea GS3A promoter element or a portion of said GS3A promoter element, that confers vasculature-specific expression in the leaf, stem and root of a mature plant to an operably associated coding sequence wherein said element is operably joined to sequences not naturally associated with said element.

7. A recombinant DNA molecule of claim 6 in which the GS3A glutamine synthetase promoter element is an element having a nucleotide sequence as depicted in SEQ ID NO:2 from nucleotide residue number 1701 to 1832 or a portion of said depicted sequence.

8. A recombinant DNA molecule of claim 6 in which the GS3A glutamine synthetase promoter element is an element having a nucleotide sequence as depicted in SEQ ID NO:2 from nucleotide residue number 1704 to 1736 or a portion of said depicted sequence, wherein said depicted sequence is:
AATTCAATTGATCTAG-
TAGATAAAAAGATTCTC.

9. A recombinant DNA molecule of claim 6 in which the GS3A glutamine synthetase promoter element is an element having a nucleotide sequence as depicted in SEQ ID NO:2 from nucleotide residue number 1704 to 1727 or a portion of said depicted sequence, wherein said depicted sequence is:
AATTCAATTGATCTAGTAGATAAA.

10. The recombinant DNA molecule of claim 6 in which the GS3A glutamine synthetase promoter element is an element having a nucleotide sequence as depicted in SEQ ID NO:2 from nucleotide residue number 1711 to 1727 or a portion of said depicted sequence, wherein said depicted sequence is:
TTGATCTAGTAGATAAA.

11. A recombinant gene construct comprising a GS3A glutamine synthetase promoter element operably associated with a nucleotide sequence which encodes a heterologous gene product, wherein said element is a pea GS3A promoter element or a portion of the pea GS3A promoter element, that confers vasculature-specific expression in the leaf, stem and root of a mature plant to the operably associated coding sequence and wherein said element is operably joined to sequences not naturally associated with said element.

12. A recombinant gene construct of claim 11 in which the GS3A glutamine synthetase promoter element is an element having a nucleotide sequence as depicted in SEQ ID NO:2 from nucleotide residue number 1701 to 1832 or a portion of said depicted sequence.

13. A recombinant gene construct of claim 11 in which the GS3A glutamine synthetase promoter element is an element having a nucleotide sequence as depicted in SEQ ID NO:2 from nucleotide residue number 1704 to 1736 or a portion of said depicted sequence, wherein said depicted sequence is:
AATTCAATTGATCTAG-
TAGATAAAAAGATTCTC.

14. A recombinant gene construct of claim 11 in which the GS3A glutamine synthetase promoter element is an element having a nucleotide sequence as depicted in SEQ ID NO:2 from nucleotide residue number 1704 to 1727 or a portion of said depicted sequence, wherein said depicted sequence is:
AATTCAATTGATCTAGTAGATAAA.

15. A recombinant gene construct of claim 11 in which the GS3A glutamine synthetase promoter element is an element having a nucleotide sequence as depicted in SEQ ID NO:2 from nucleotide residue number 1711 to 1727 or a portion of said depicted sequence, wherein said depicted sequence is:
TTGATCTAGTAGATAAA.

16. A transgenic plant containing a transgene controlled by a GS3A glutamine synthetase promoter element which is a pea GS3A promoter element or a portion of the pea GS3A promoter element, that confers vasculature-specific expression in the leaf, stem and root of a mature plant to said transgene wherein said element is operably joined to sequences not naturally associated with said element.

17. A transgenic plant of claim 16 in which the GS3A glutamine synthetase promoter element is an element having a nucleotide sequence as depicted in SEQ ID NO:2 from nucleotide residue number 1701 to 1832 or a portion of said depicted sequence.

18. A transgenic plant of claim 16 in which the GS3A glutamine synthetase promoter element is an element having a nucleotide sequence as depicted in SEQ ID NO:2 from nucleotide residue number 1704 to 1736 or a portion of said depicted sequence, wherein said depicted sequence is:
AATTCAATTGATCTAG-
TAGATAAAAAGATTCTC.

19. A transgenic plant of claim 16 in which the GS3A glutamine synthetase promoter element is an element having a nucleotide sequence as depicted in SEQ ID NO:2 from nucleotide residue number 1704 to 1727 or a portion of said depicted sequence, wherein said depicted sequence is:
AATTCAATTGATCTAGTAGATAAA.

20. A transgenic plant of claim 16 in which the GS3A glutamine synthetase promoter element is an element having a nucleotide sequence as depicted in SEQ ID NO:2 from nucleotide residue number 1711 to 1727 or a portion of said depicted sequence, wherein said depicted sequence is:
TTGATCTAGTAGATAAA.

21. The transgenic plant of claim 16 in which the transgene encodes a product that renders the plant resistant to viral infection.

22. The transgenic plant of claim 21 in which the transgene comprises a nucleotide sequence which encodes a viral coat protein.

23. The transgenic plant of claim 16 in which the transgene encodes a product that renders the plant resistant to a herbicide.

24. A substantially pure GS3B glutamine synthetase promoter element which is a pea GS3B promoter element or a portion of the pea GS3B promoter element, that confers vasculature-specific expression in the leaf stem and root of a mature plant to an operably associated coding sequence wherein said element is operably joined to sequences not naturally associated with said element.

25. A recombinant DNA molecule containing a GS3B glutamine synthetase promoter element which, wherein GSPE is a pea GS3B promoter element or a portion of the pea GS3B promoter element, that confers vasculature-specific expression in the leaf, stem and root of a mature plant to an operably associated coding sequence wherein said element is operably joined to sequences not naturally associated with said element.

26. A recombinant gene construct comprising a GS3B glutamine synthetase promoter element operably associated with a nucleotide sequence which encodes a heterologous gene product, wherein said element is a pea GS3B promoter element or a portion of the pea GS3B promoter element, that confers vasculature-specific expression in the leaf, stem and root of a mature plant to the operably associated coding sequence and wherein said element is operably joined to sequences not naturally associated with said element.

27. A transgenic plant containing a transgene controlled by a GS3B glutamine synthetase promoter element (GSPE), wherein GSPE is a pea GS3B promoter element or a portion of the pea GS3B promoter element, that confers vasculature-specific expression in the leaf, stem and root of a mature plant to said transgene wherein said element is operably joined to sequences not naturally associated with said element.

28. The transgenic plant of claim 27 in which the transgene encodes a product that renders the plant resistant to viral infection.

29. The transgenic plant of claim 28 in which the transgene comprises a nucleotide sequence which encodes a viral coat protein.

30. The transgenic plant of claim 27 in which the transgene encodes a product that renders the plant resistant to a herbicide.

* * * * *